US011285318B2

(12) United States Patent
Tai

(10) Patent No.: US 11,285,318 B2
(45) Date of Patent: Mar. 29, 2022

(54) PERIPHERAL NEUROMODULATION TO TREAT BLADDER AND BOWEL DYSFUNCTION

(71) Applicant: University of Pittsburgh—Of the Commonwealth System of Higher Education, Pittsburgh, PA (US)

(72) Inventor: Changfeng Tai, Wexford, PA (US)

(73) Assignee: University of Pittsburgh—Of the Commonwealth System of Higher Education, Pittsburgh, PA (US)

( * ) Notice: Subject to any disclaimer, the term of this patent is extended or adjusted under 35 U.S.C. 154(b) by 112 days.

(21) Appl. No.: 16/609,883

(22) PCT Filed: May 2, 2018

(86) PCT No.: PCT/US2018/030640
§ 371 (c)(1),
(2) Date: Oct. 31, 2019

(87) PCT Pub. No.: WO2018/204492
PCT Pub. Date: Nov. 8, 2018

(65) Prior Publication Data
US 2020/0069940 A1 Mar. 5, 2020

Related U.S. Application Data

(60) Provisional application No. 62/501,351, filed on May 4, 2017.

(51) Int. Cl.
*A61N 1/36* (2006.01)
*A61N 1/04* (2006.01)

(52) U.S. Cl.
CPC ....... *A61N 1/36007* (2013.01); *A61N 1/0456* (2013.01); *A61N 1/36034* (2017.08)

(58) Field of Classification Search
CPC .................. A61N 1/36007; A61N 1/36034
USPC ........................................... 607/40
See application file for complete search history.

(56) References Cited

U.S. PATENT DOCUMENTS

| 3,881,494 | A | 5/1975 | Paul, Jr. |
|---|---|---|---|
| 3,902,502 | A | 9/1975 | Liss et al. |
| 5,273,033 | A | 12/1993 | Hoffman |
| 7,047,078 | B2 | 5/2006 | Boggs, II et al. |
| 9,623,243 | B2 | 4/2017 | Chancellor et al. |
| 9,878,154 | B2 | 1/2018 | Tai |
| 2013/0006322 | A1* | 1/2013 | Tai ............... A61N 1/36007 607/39 |
| 2014/0172053 | A1 | 6/2014 | Glukhovsky et al. |
| 2014/0316497 | A1 | 10/2014 | Gaunt et al. |

(Continued)

OTHER PUBLICATIONS

De Groat et al., "Reflexes to Sacral Parasympathetic Neurones Concerned with Micturition in the Cat", J. Physiol., 1969, pp. 87-108, vol. 200.

(Continued)

*Primary Examiner* — Nadia A Mahmood
(74) *Attorney, Agent, or Firm* — The Webb Law Firm

(57) ABSTRACT

Provided herein are methods for treating underactive bladder, urinary retention, detrusor-sphincter dyssynergia after spinal cord injury, constipation, and/or infrequent bowel movements including the step of applying electrical stimulation to one or more peripheral nerves.

20 Claims, 33 Drawing Sheets

(56) References Cited

U.S. PATENT DOCUMENTS

| | | | | |
|---|---|---|---|---|
| 2015/0148878 | A1* | 5/2015 | Yoo | A61N 1/0556 607/118 |
| 2016/0023005 | A1* | 1/2016 | Perryman | A61N 1/37229 607/60 |
| 2016/0045731 | A1 | 2/2016 | Simon et al. | |
| 2016/0339239 | A1 | 11/2016 | Yoo et al. | |
| 2017/0361091 | A1* | 12/2017 | Tai | A61K 31/428 |

OTHER PUBLICATIONS

De Groat et al., "Organization of the neural switching circuitry underlying reflex micturition", Acta Physiol (Oxf), 2013, pp. 66-84, vol. 207, No. 1.

Ferroni et al., "Transcutaneous Electrical Nerve Stimulation of the Foot: Results of a Novel At-home, Noninvasive Treatment for Nocturnal Enuresis in Children", Urology, 2017, pp. 80-84, vol. 101.

Lyon et al., "Pudendal but not tibial nerve stimulation inhibits bladder contractions induced by stimulation of pontine micturition center in cats", Am J Physiol Regul Integr Comp Physiol, 2016, R366-R374, vol. 310.

Moazzam et al., "Inhibition and Excitation of Bladder Function by Tibial Nerve Stimulation Using a Wirelessly Powered Implant: An Acute Study in Anesthetized Cats", The Journal of Urology, 2016, pp. 926-933, vol. 196.

Sato et al., "Reflex Bladder Activity Induced by Electrical Stimulation of Hind Limb Somatic Afferents in the Cat", Journal of the Autonomic Nervous System, 1980, pp. 229-241, vol. 1.

Tai et al., "Prolonged postslimulation inhibition of bladder activity induced by tibial nerve stimulation in cats", Am J Physiol Renal Physiol, 2011, pp. F385-F392, vol. 300.

Tai et al., "Differential role of opiod receptors in tibial nerve inhibition of nocicepetive and nonnociceptive bladder reflexes in cats", Am J Physiol Renal Physiol, 2012, pp. F1090-F1097, vol. 302.

* cited by examiner

PERIPHERAL NEUROMODULATION TO TREAT BLADDER AND BOWEL DYSFUNCTION

CROSS-REFERENCE TO RELATED APPLICATIONS

The present application is the United States national phase of International Application No. PCT/US2018/030640 filed May 2, 2018, and claims the benefit of United States Provisional Patent Application No. 62/501,351, filed May 4, 2017, the contents of each of which are incorporated by reference herein in their entirety.

STATEMENT REGARDING FEDERALLY SPONSORED RESEARCH

This invention was made with government support under DK094905, DK102427, and DK111382 awarded by the National Institutes of Health. The government has certain rights in the invention.

BACKGROUND OF THE INVENTION

Field of the Invention

The present invention relates to methods for treating physiological disorders using electrical stimulation.

More particularly, the present invention relates to invasive and non-invasive methods for treating underactive bladder (UAB), urinary retention, detrusor-sphincter dyssynergia after spinal cord injury, constipation, and/or infrequent bowel movements with electrical stimulation of peripheral nerves.

Description of Related Art

Underactive bladder (UAB) is a symptom complex suggestive of detrusor underactivity and characterized by prolonged urination time with or without a sensation of incomplete bladder empting, usually with hesitancy, reduced sensation on filling, and a slow stream. The prevalence of UAB is about 25-40% in the population of individuals 60 years old and above, and as many as 48% of the older men and 45% of older women show detrusor underactivity during urological evaluation. The impact of severe UAB on quality of life is significant, requiring intermittent self-catheterization or an indwelling suprapubic catheter to drain the bladder when urinary retention occurs. Currently, it is a therapeutic challenge for clinicians to successfully treat UAB, leaving the majority of UAB patients untreated; however, UAB in comparison to overactive bladder syndrome (OAB) has been the focus of relatively few basic science studies.

Accordingly, there is a need in the art for effective methods for treating UAB, urinary retention, detrusor-sphincter dyssynergia after spinal cord injury, constipation, and/or infrequent bowel movements.

SUMMARY OF THE INVENTION

Accordingly, provided herein are methods of treating UAB, urinary retention, and/or detrusor-sphincter dyssynergia after spinal cord injury through use of electrical stimulation of the superficial peroneal nerve.

Also provided herein are methods of treating infrequent bowel movements and/or constipation through use of electrical stimulation of the superficial peroneal nerve.

Further provided herein are methods of treating UAB, urinary retention, and/or detrusor-sphincter dyssynergia after spinal cord injury through use of electrical stimulation of one or more of the deep peroneal nerve, tibial nerve, medial plantar nerve, lateral plantar nerve, saphenous nerve, sural nerve, and/or femoral cutaneous nerve.

Also provided herein are methods of treating infrequent bowel movements and/or constipation through use of electrical stimulation of one or more of the deep peroneal nerve, tibial nerve, medial plantar nerve, lateral plantar nerve, saphenous nerve, sural nerve, and/or femoral cutaneous nerve.

Figure 7:
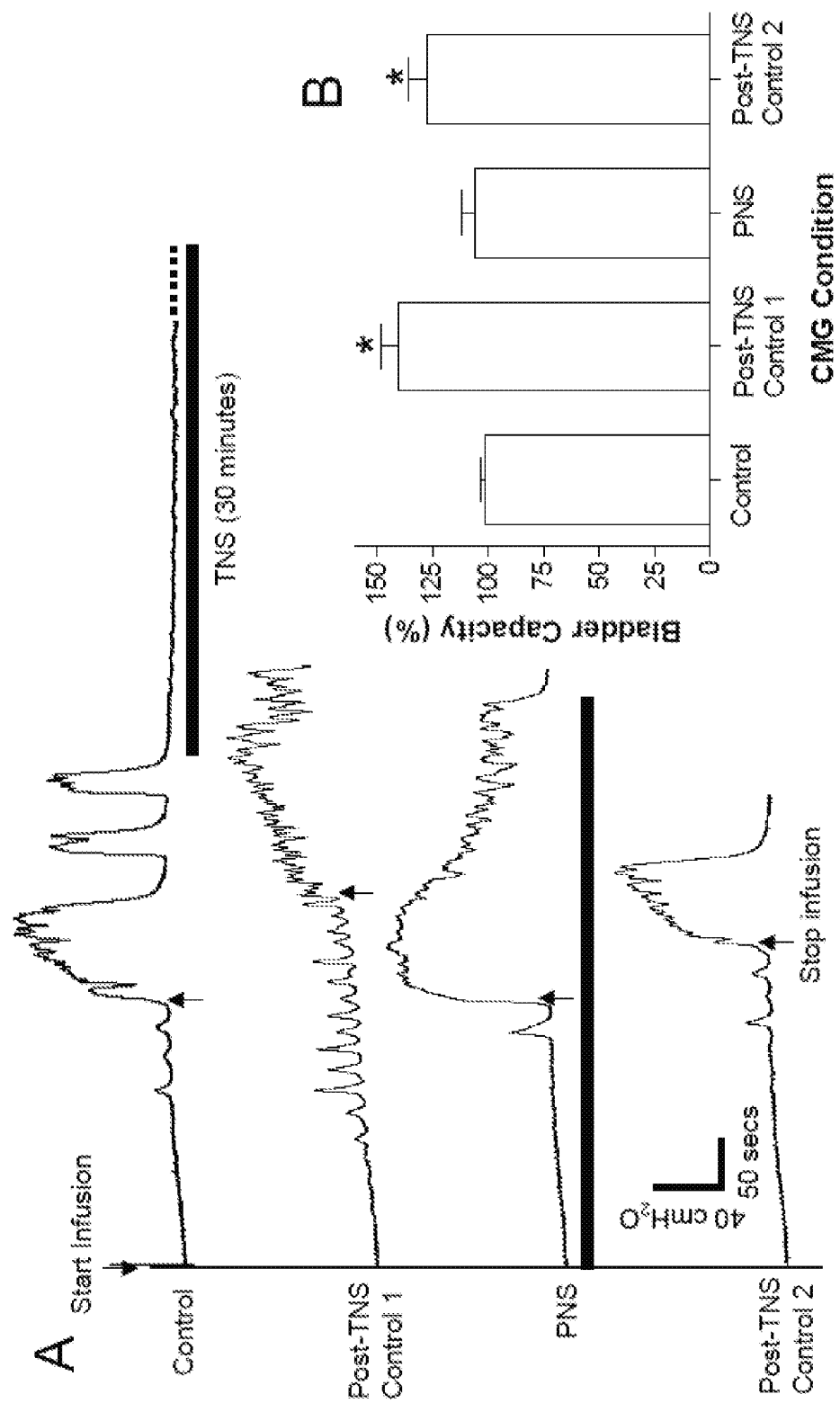

FIG. 7. Superficial peroneal nerve stimulation (PNS) removed the post-stimulation inhibition induced by tibial nerve stimulation (TNS). A: Repeated CMG tracings showing that 30-minute TNS (5 Hz, 0.2 ms, 4T=1.2 V) produced long-lasting post-stimulation inhibition that was completely removed when PNS (1 Hz, 0.2 ms, 1T=1.4 V) was applied. T—threshold intensity to induce observable toe twitch (TNS) or muscle twitch on the posterior thigh (PNS). The black bar under the bladder pressure tracing indicates the duration of TNS or PRS. Infusion rate=3 ml/min B: Summarized results (N=5 cats). The bladder capacity was normalized to the control capacity. * significantly ($p<0.01$) different from the control or PNS (one-way ANOVA). TNS (5 Hz, 0.2 ms, 3-4T, T=0.3-1.2 V), PNS (1-3 Hz, 0.2 ms, 1-4T, 1T=1.4-12 V).

Figure 8:
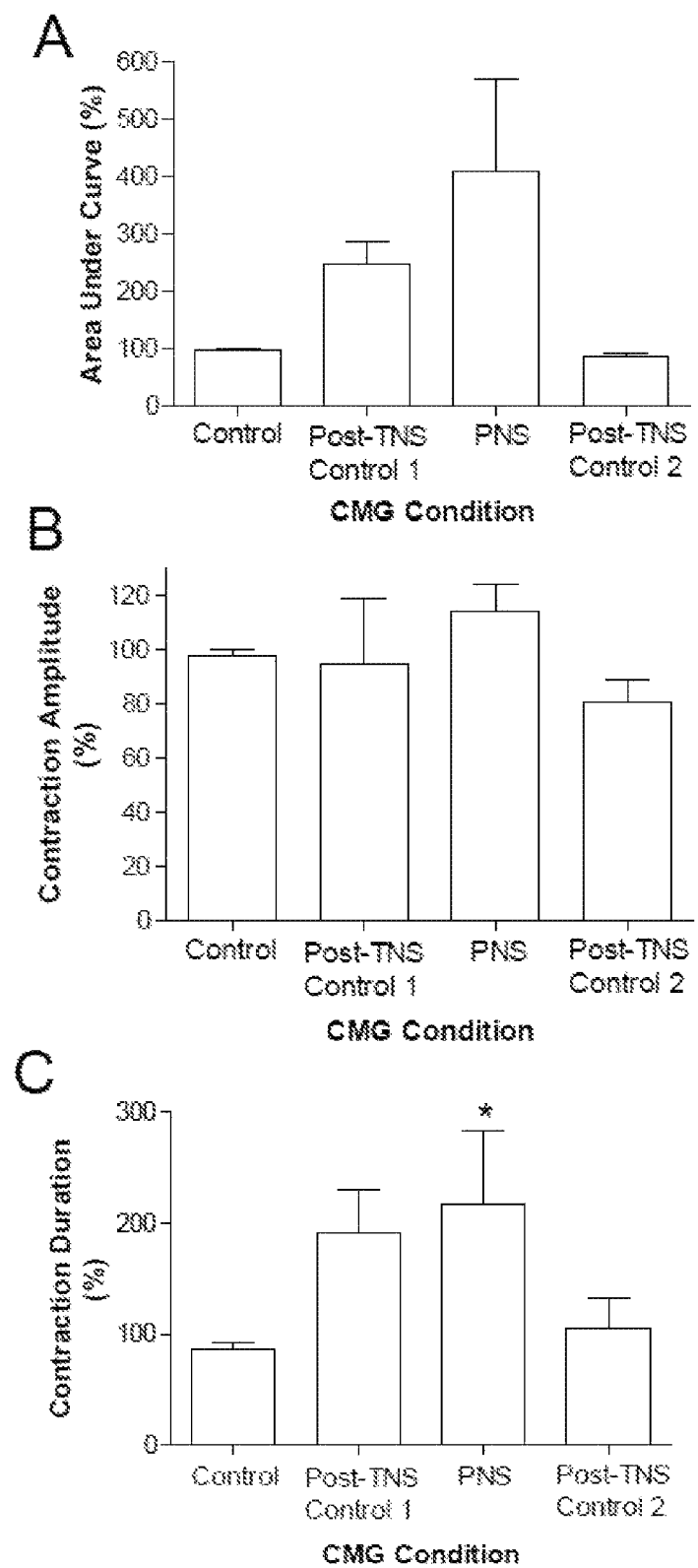

FIG. 8. Effects of tibial nerve stimulation (TNS) and superficial peroneal nerve stimulation (PNS) on bladder contraction. A: Area under the curve of bladder contraction pressure. B: Contraction amplitude. C: Contraction duration. Bladder contraction response was normalized to the control response. * significantly ($p<0.05$) different control response (one-way ANOVA, N=4 cats). TNS (5 Hz, 0.2 ms, 3-4T, T=0.3-1.2 V), PNS (1-3 Hz, 0.2 ms, 1-4T, 1T=1.4-8 V). T—threshold intensity to induced observable toe twitch (TNS) or muscle twitch on the posterior thigh (PNS).

Figure 9:
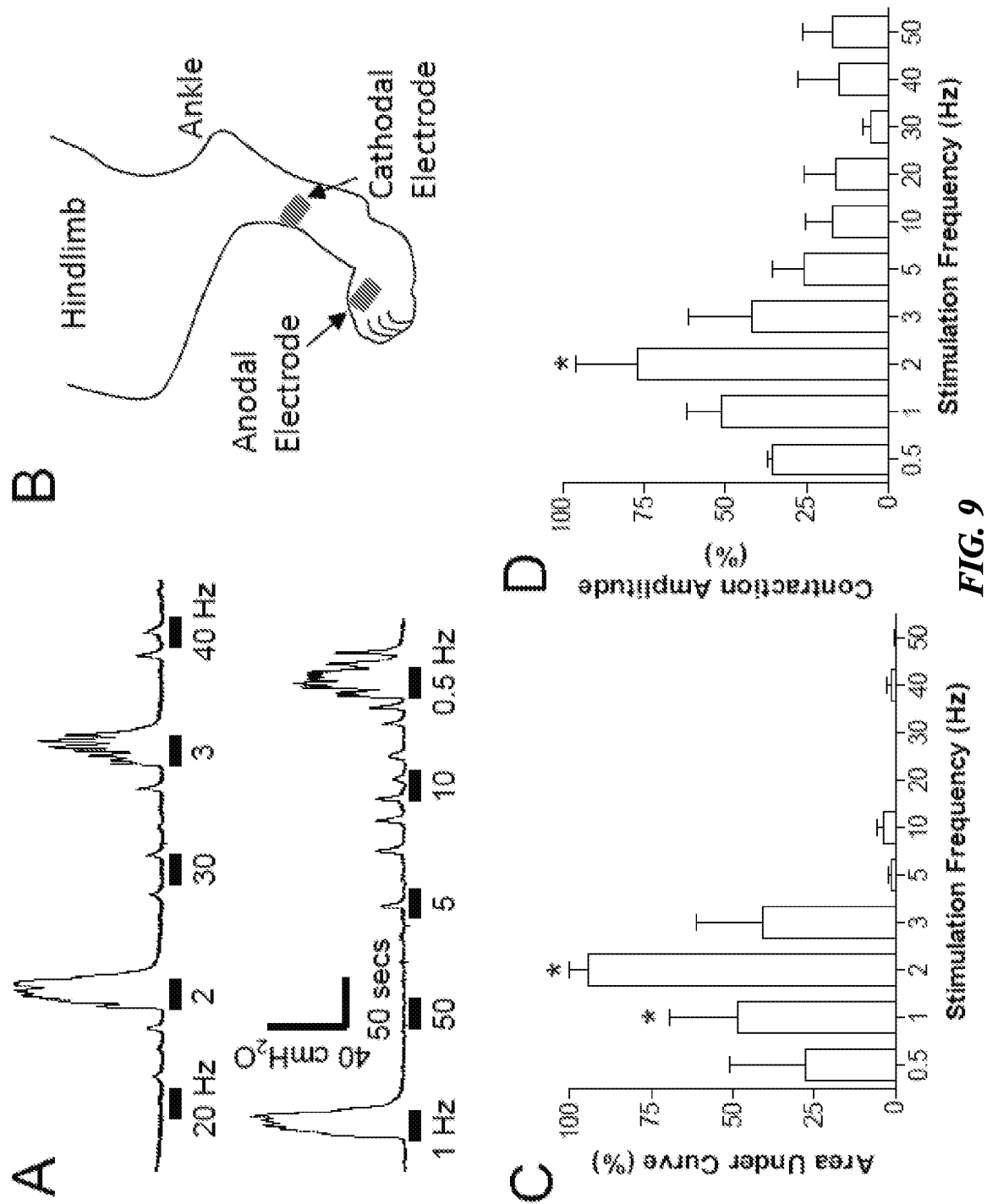

FIG. 9. Bladder pressure responses to different frequencies (0.5-50 Hz) of transcutaneous foot stimulation. A: Bladder pressure tracings. The black bar under the pressure tracing indicates the duration (30 secs) of foot stimulation (0.2 ms, 2T=11.6 V). T—threshold intensity to induce observable toe twitch or muscle twitch on the posterior thigh. B: Locations of the skin surface electrodes that were attached on the dorsal side of the foot to stimulate the peroneal nerve and its branches. C: Normalized area under curve. D. Normalized contraction amplitude. Bladder pressure response was normalized to the maximal response in each animal (N=3 cats). * significant ($p<0.05$) different from the response at 50 Hz (one-way ANOVA). Foot stimulation (0.2 ms, 2-4T, T=3-7 V).

Figure 10:
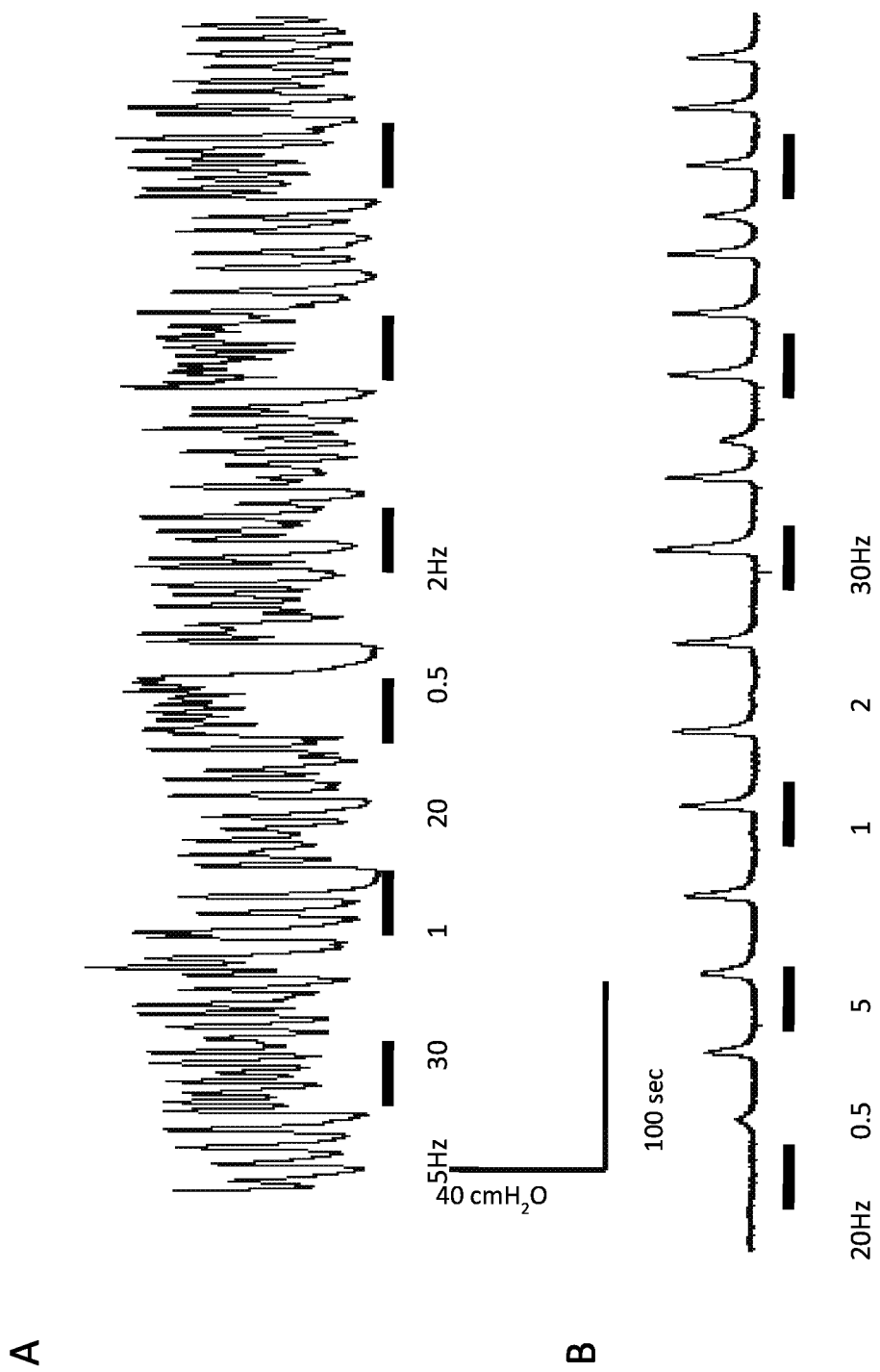

FIG. 10. Bladder pressure responses to different frequencies (0.5-30 Hz) of Saphenous Nerve Stimulation (SNS). A: Bladder pressure tracings. The black bar under the pressure tracing indicates the duration (30 secs) of SNS (0.2 ms, 3T, T=2.2V). (N=2 cats). T threshold intensity to induce muscle twitch at the back thigh. B: Another bladder pressure tracings. The black bar under the pressure tracing indicates the duration (30 secs) of SNS (0.2 ms, 2T, T=5V), (N=3 cats).

Figure 11:
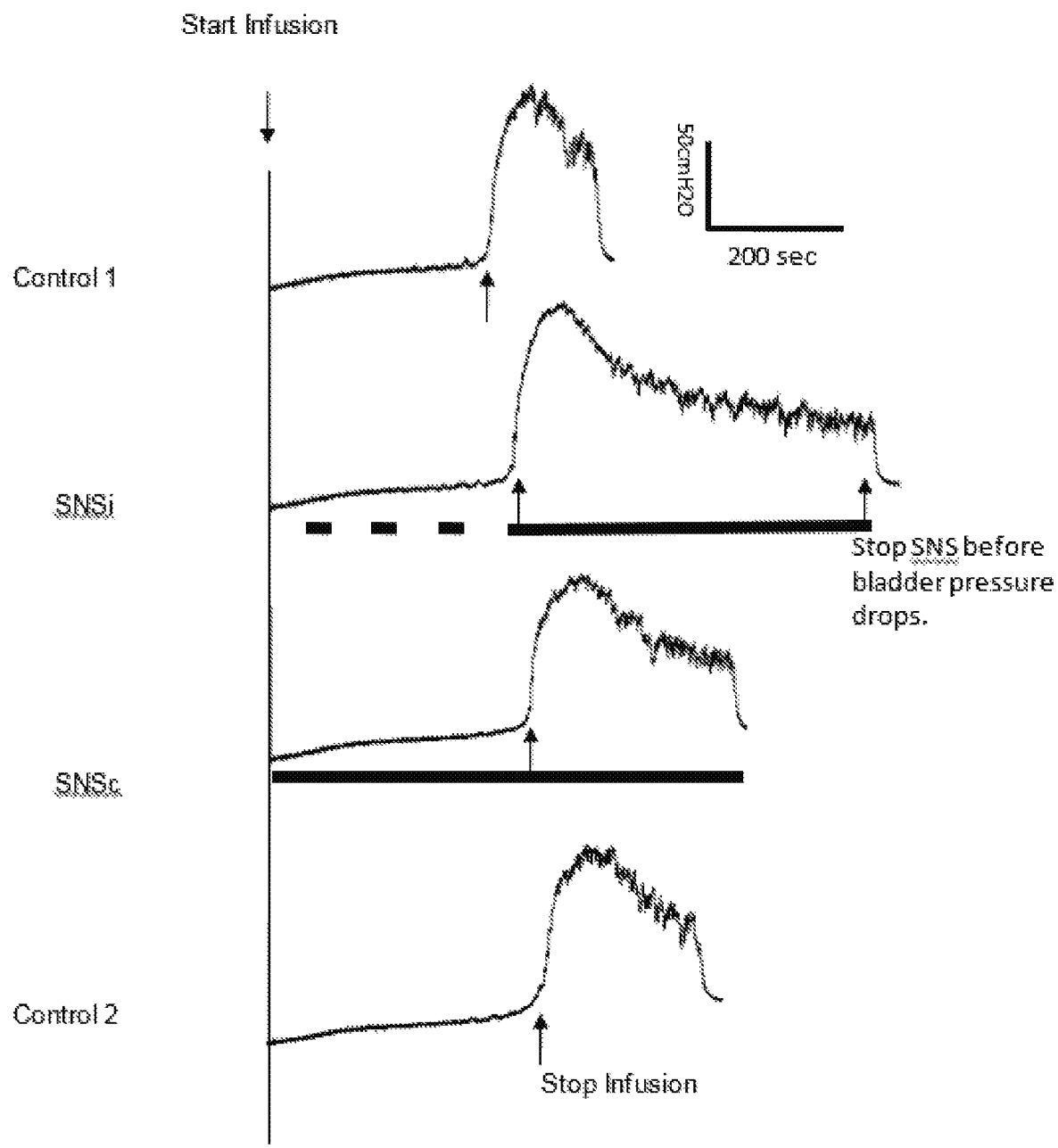

FIG. 11. Effect of saphenous nerve stimulation (SNS) on bladder capacity. Repeated CMG tracings with/without SNS. (infusion rate: 3 ml/min, 1 Hz, 0.2 ms, 4T=7V.). SNSi—intermittent SNS. SNSc—continuous SNS.

Figure 12:
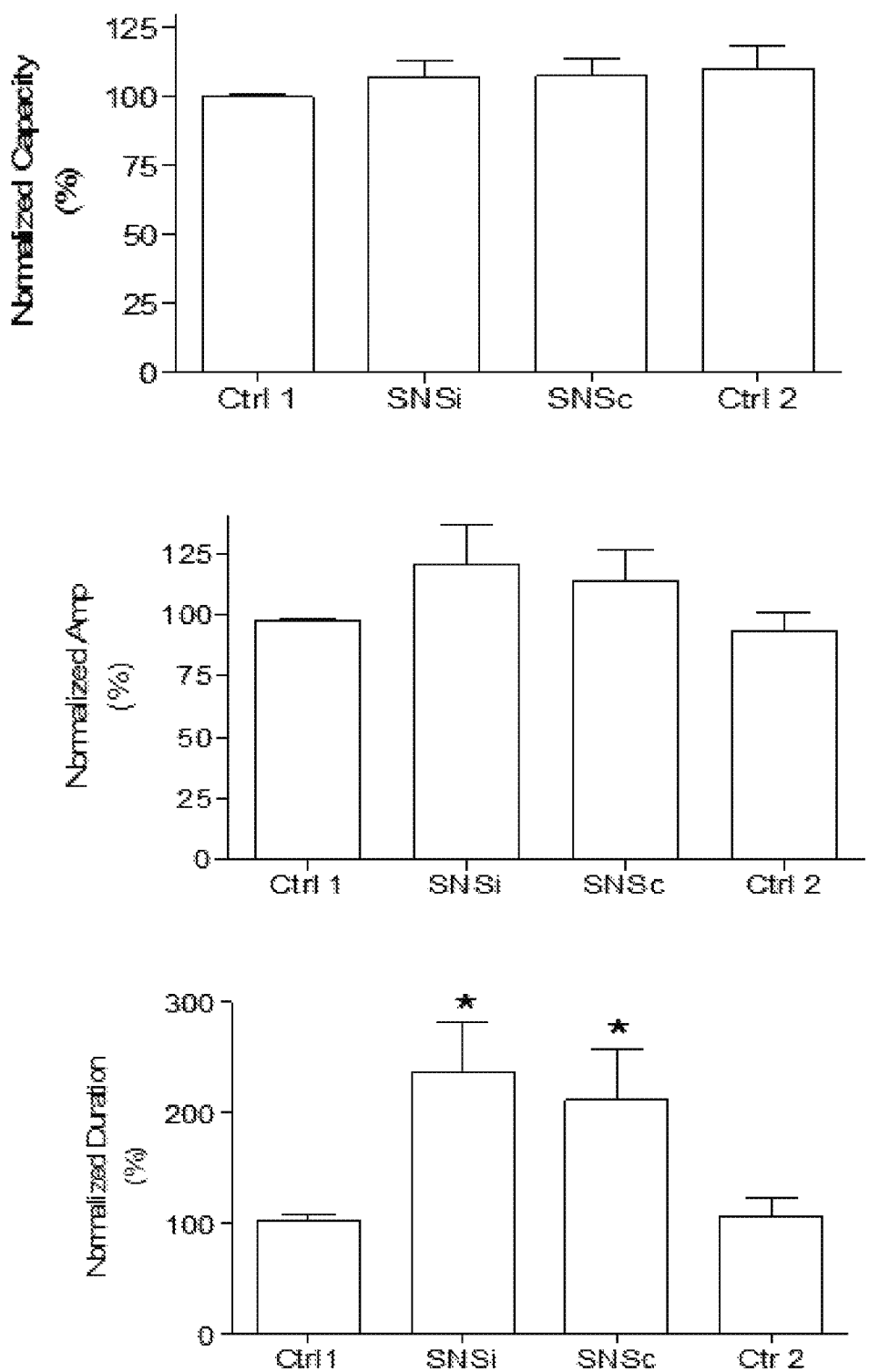

FIG. 12. Effect of Saphenous nerve stimulation (SNS) on bladder capacity. Repeated CMG was normalized to control 1 CMG. A. bladder normalized capacity, B. normalized contraction amplitude, C. normalized contraction duration. (N=6, 1 Hz, 0.2 ms, 4T=10V) * significantly ($p<0.05$) different from the control 1 (one-way ANOVA).

Figure 13:
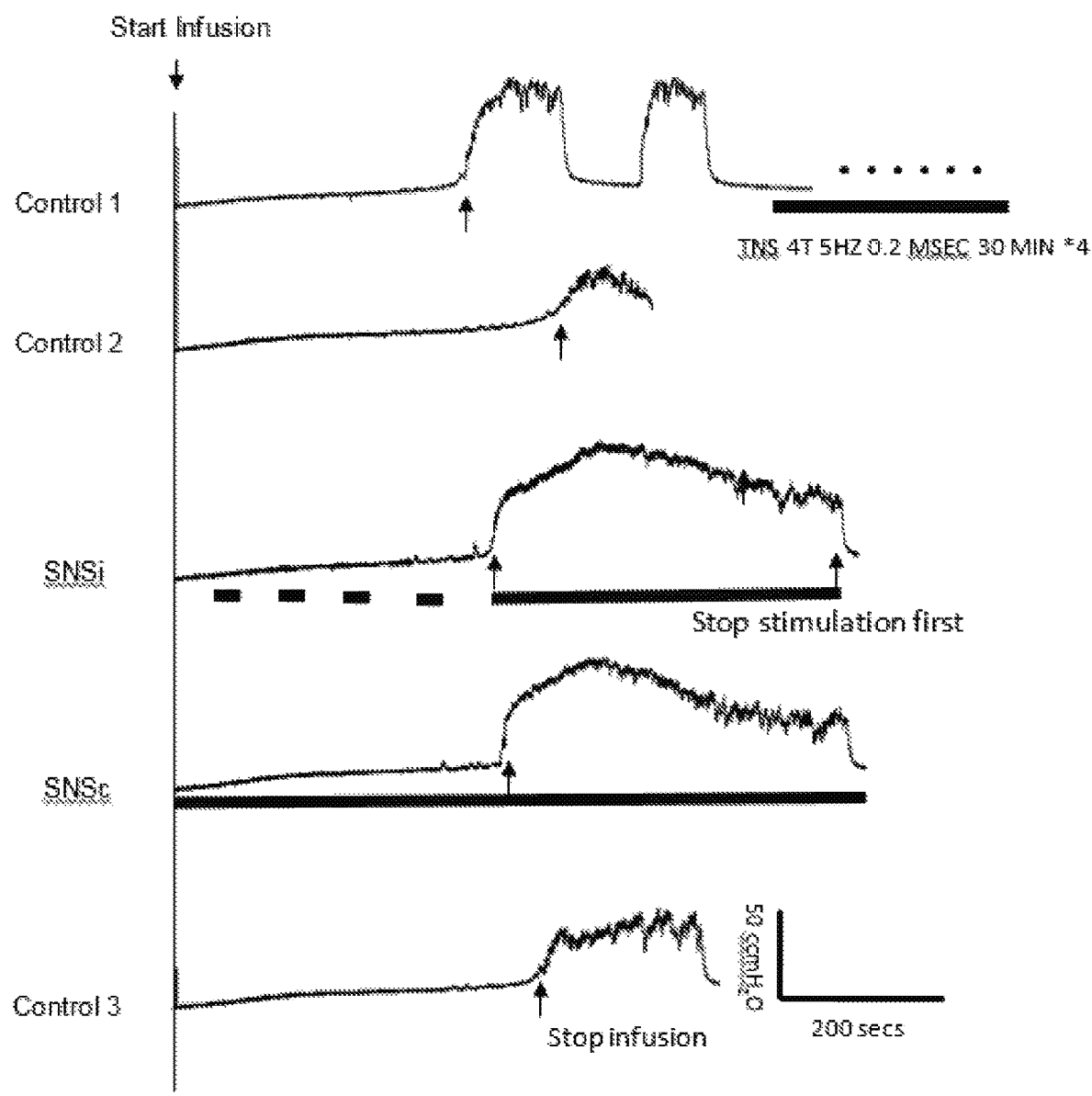

FIG. 13. Saphenous nerve stimulation (SNS) removed the post-stimulation inhibition induce by tibial nerve stimulation (TNS). CMG tracings with/without SNS (1 Hz, 0.2 ms, 2T=10 V). T—threshold intensity to induce observable muscle twitch at the back thigh for SNS, but at the toe for TNS.

Figure 14:
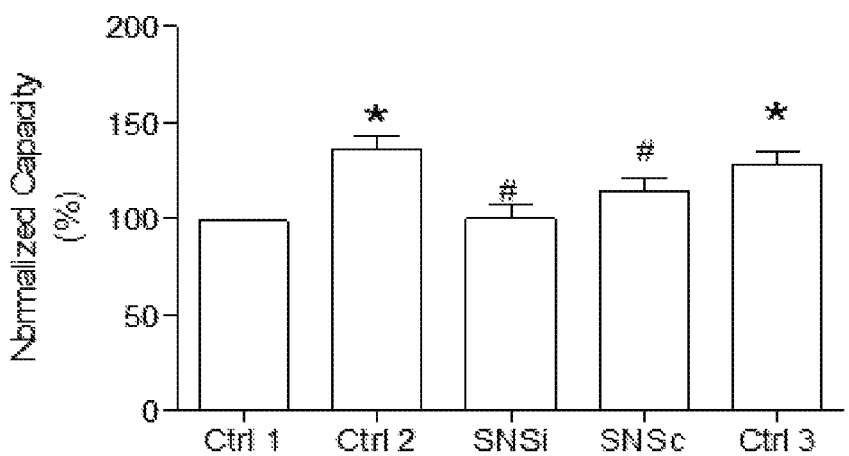
Figure 14:
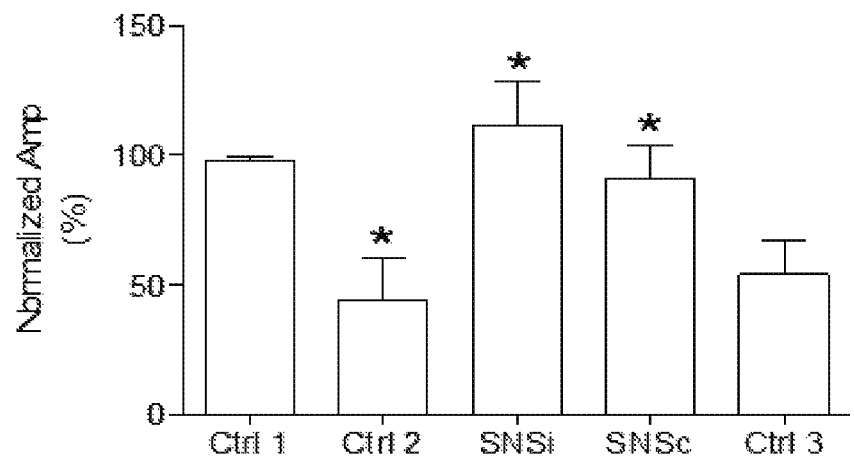
Figure 14:
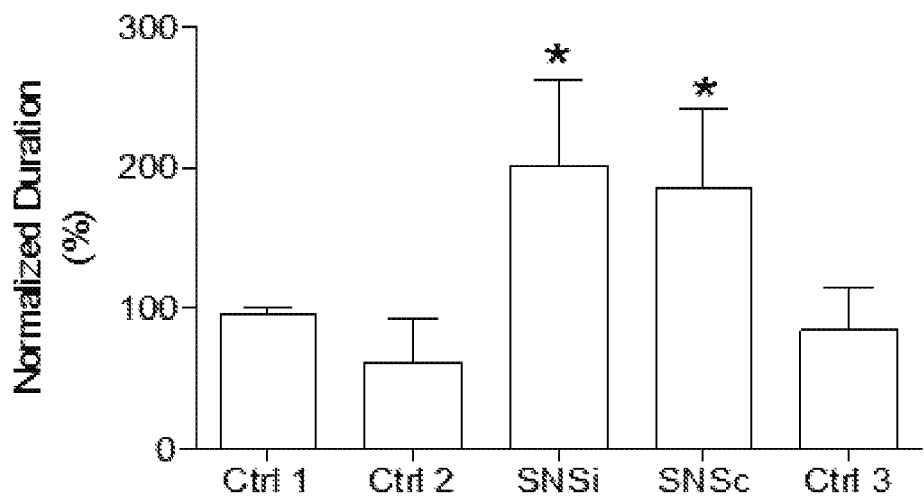

FIG. 14. Effect of saphenous nerve stimulation (SNS) on bladder capacity. A. normalized bladder capacity. B. normalized contraction amplitude. C. normalized contraction duration. (1 Hz, 0.2 ms, 4T or 10V N=6 cats, infusion rate: 2-4 ml/min). * significantly ($p<0.05$) different from the control 1. # significantly ($p<0.05$) different from the control 2 (one-way ANOVA).

Figure 15:
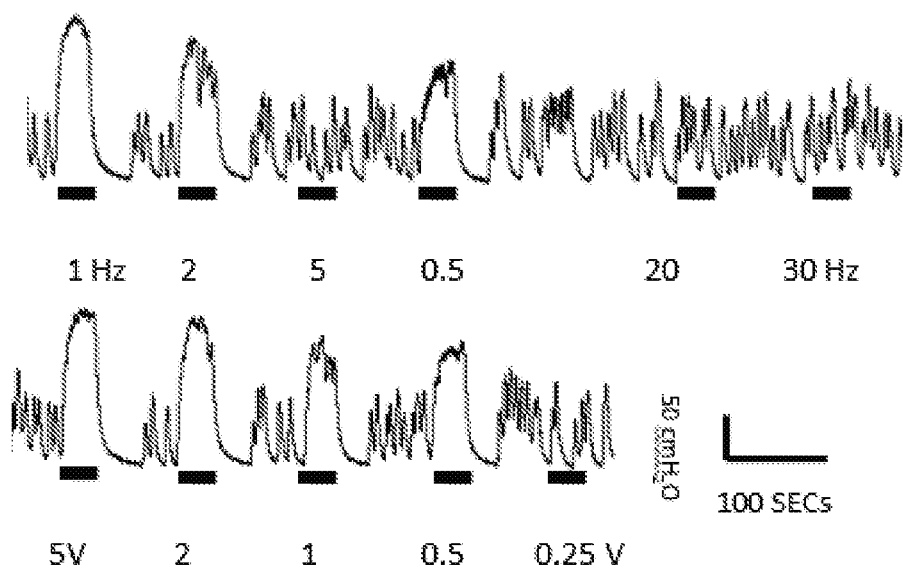
Figure 15:
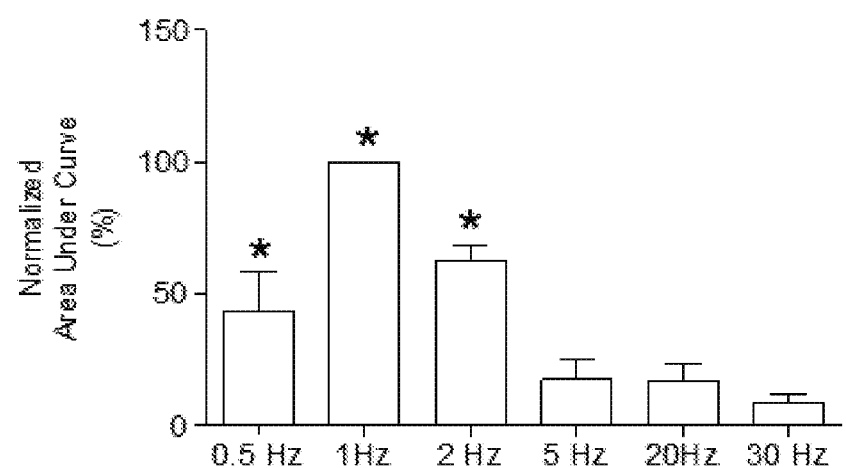
Figure 15:
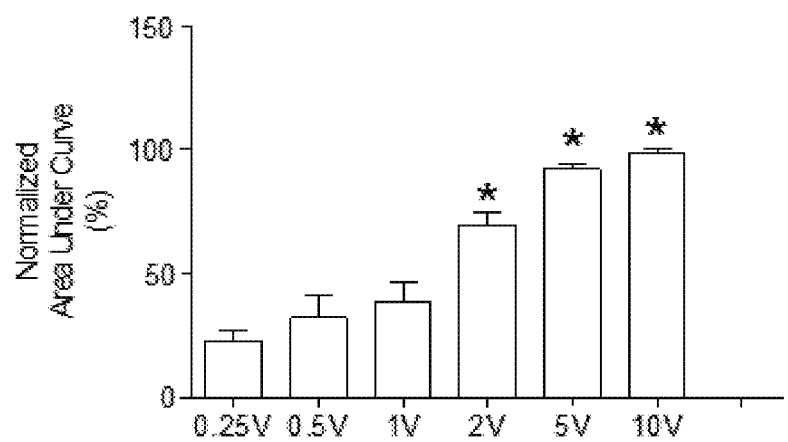

FIG. 15. Bladder pressure responses to different frequencies (0.5-30 Hz) and intensities (0.25-10V) of SNS. A: bladder pressure tracings. The black bar under the pressure tracing indicates the duration (30 secs) of SNS (0.2 ms). B: Normalized area under curve different frequencies. C: Normalized area under curve different intensities. (N=5 cats). * significantly ($p<0.05$) different from the response at 0.25V or 0.5 Hz (one-way ANOVA).

Figure 16:
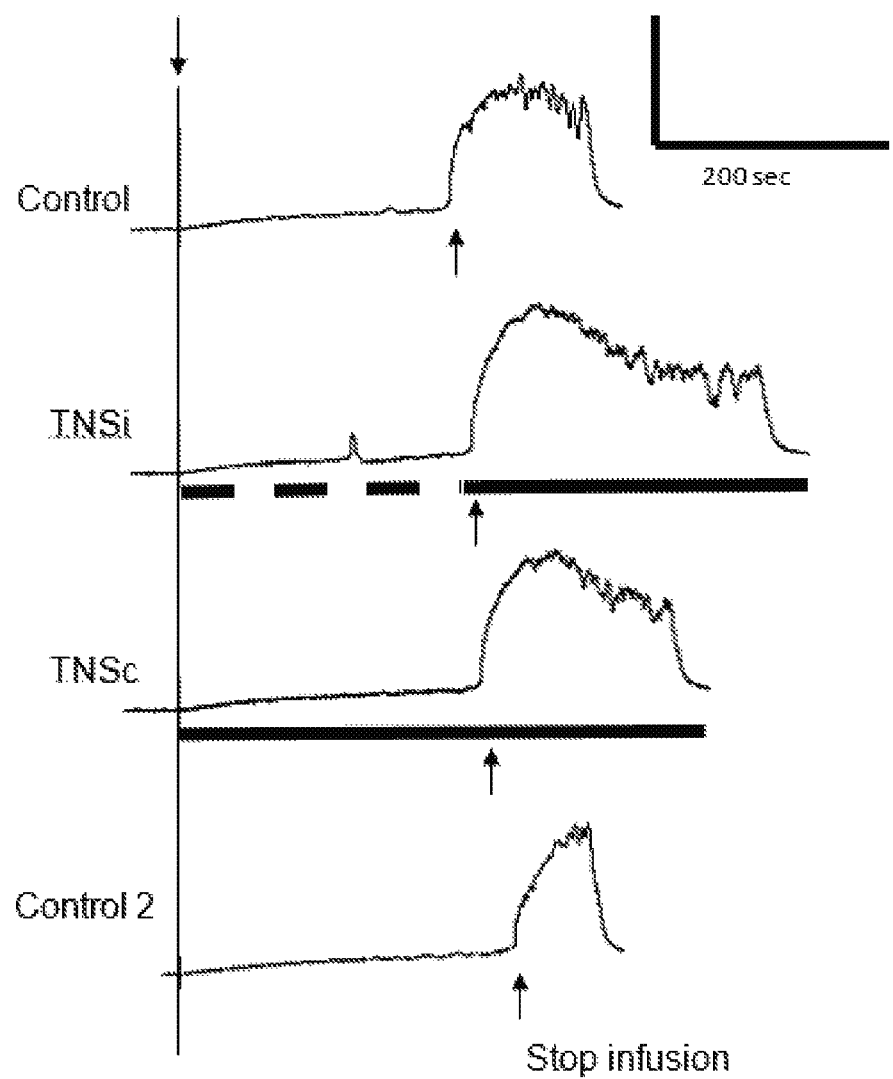
Figure 16:
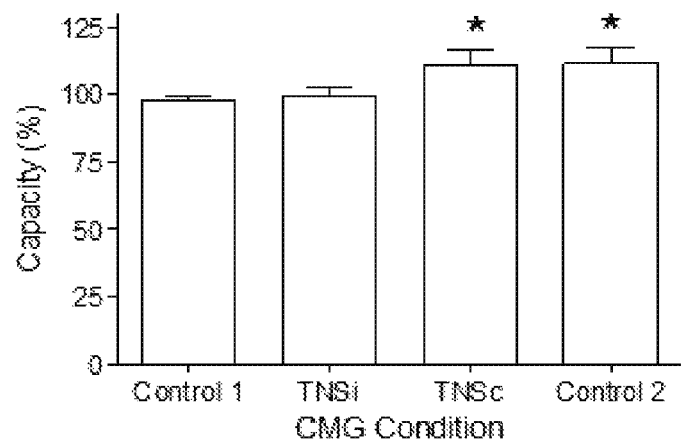

FIG. 16. Effect of tibial nerve stimulation (TNS) on bladder capacity before the bladder is in retention. TNSi—intermittent TNS. TNSc—continuous TNS. TNS (1 Hz, 0.2 ms, 1-4T). *=significantly different from control 1.

Figure 17:
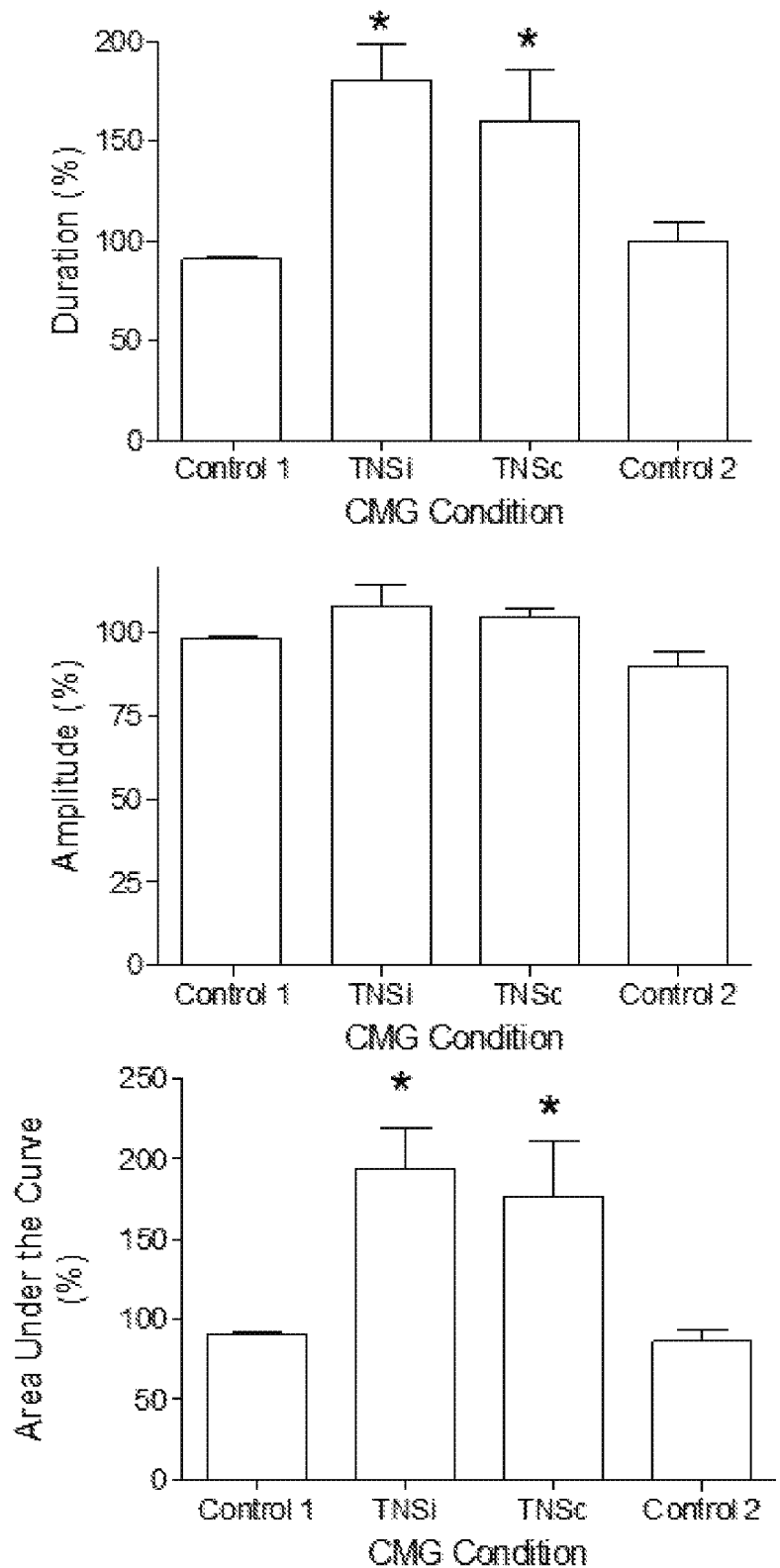

FIG. 17. Effect of tibial nerve stimulation (TNS) on micturition contraction before the bladder is in retention. TNSi—intermittent TNS. TNSc—continuous TNS. TNS (1 Hz, 0.2 ms, 1-4T).

Figure 18A:
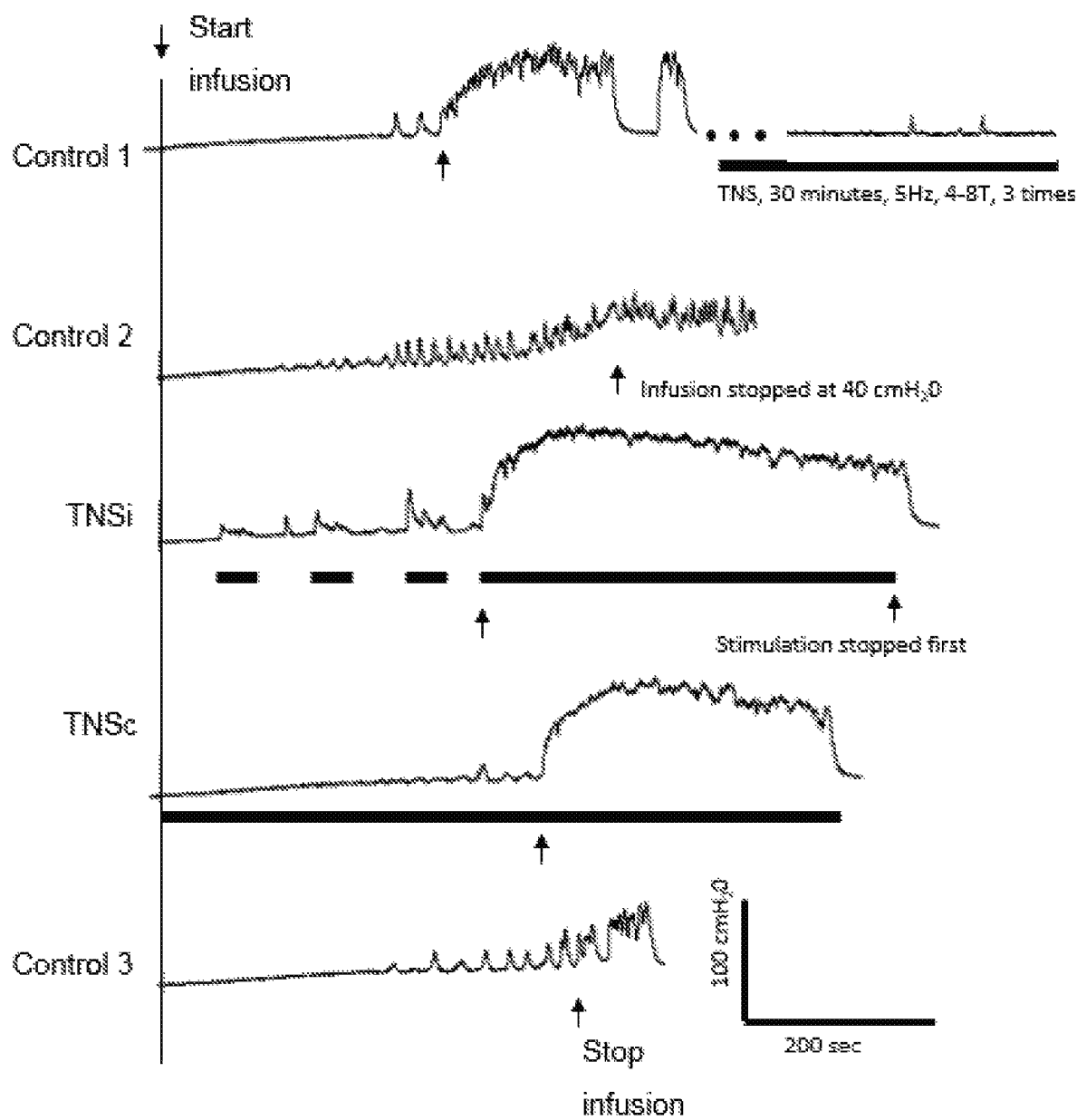
Figure 18B:
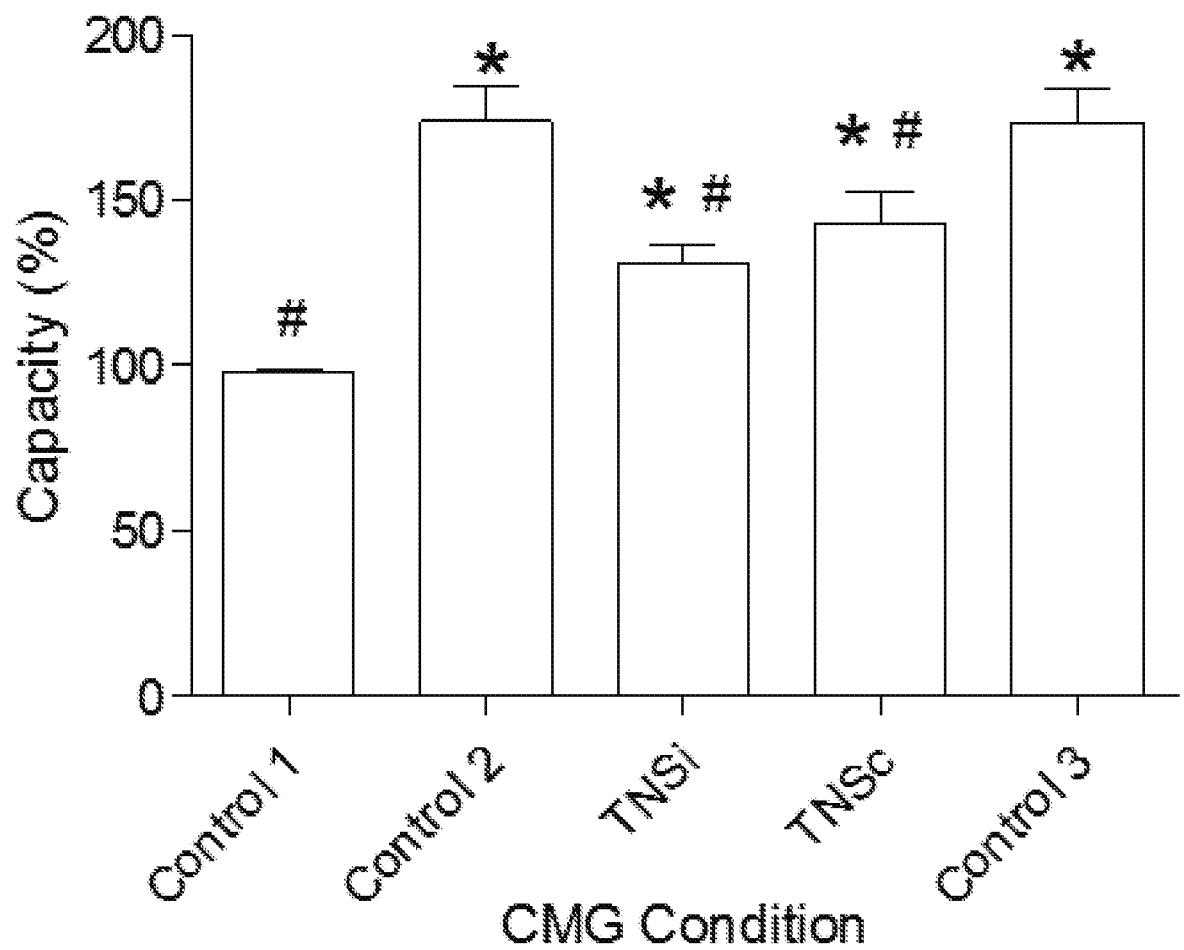

FIG. 18A-18B. Effect of tibial nerve stimulation (TNS) on bladder capacity when bladder is in retention. TNSi—intermittent TNS. TNSc—continuous TNS. TNS (1 Hz, 0.2 ms, 1-4T). *=significantly different from control 1; #=significantly different from control 2.

Figure 19:
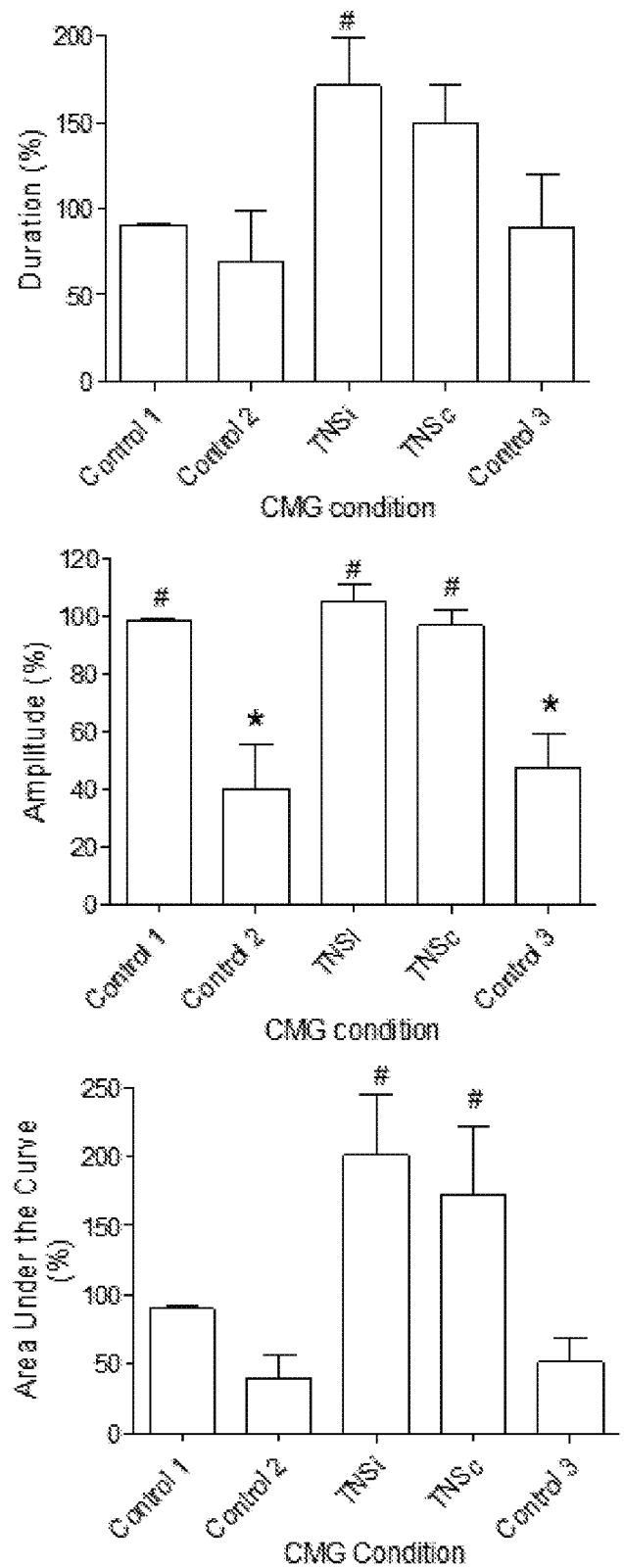

FIG. 19. Effect of tibial nerve stimulation (TNS) on micturition contraction when bladder is in retention. TNSi—intermittent TNS. TNSc—continuous TNS. TNS (1 Hz, 0.2 ms, 1-4T). *=significantly different from control 1; #=significantly different from control 2.

Figure 20:
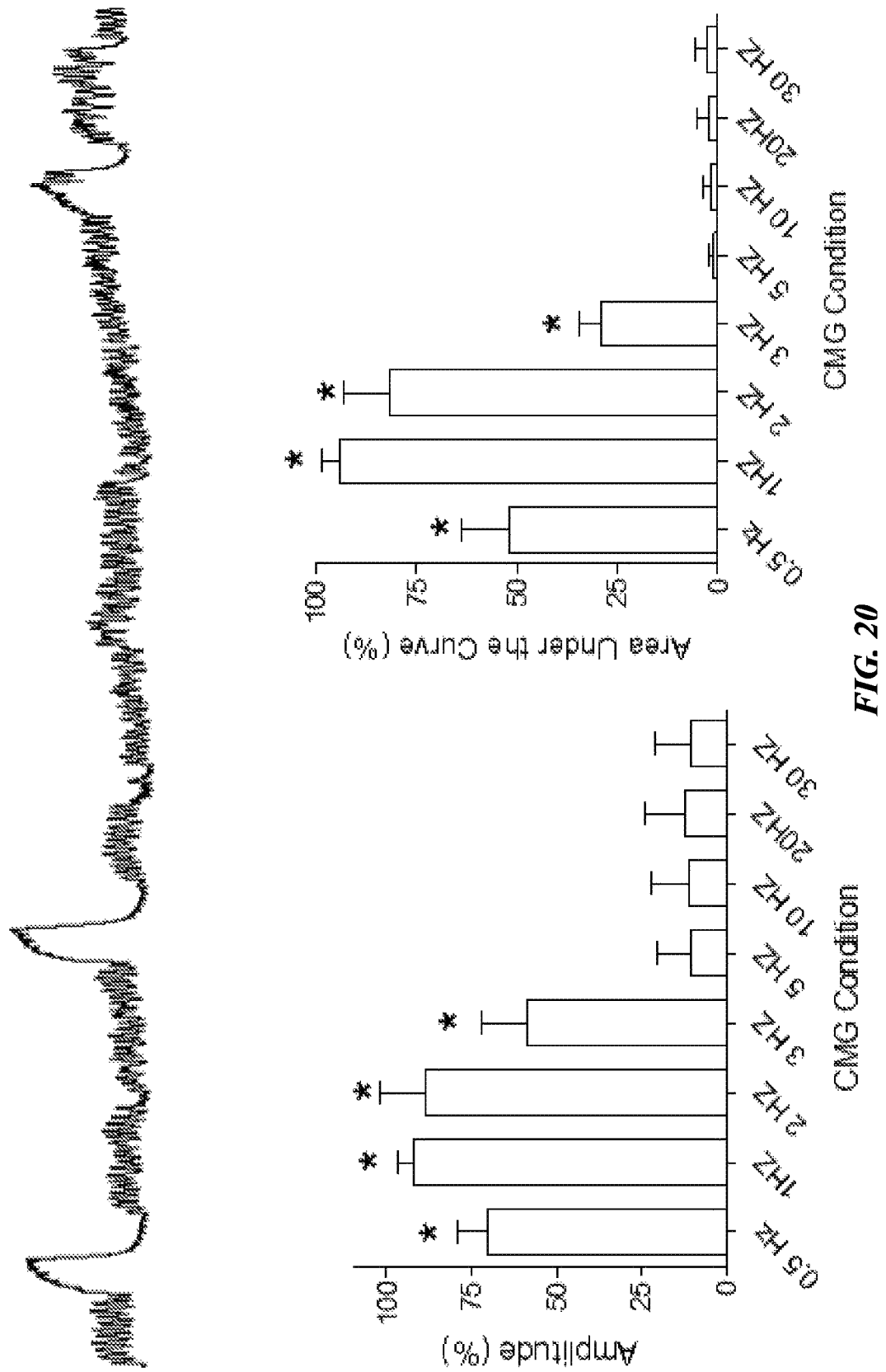

FIG. 20. Frequency responses of tibial nerve stimulation (TNS) when bladder is in retention. TNS (1 Hz, 0.2 ms, 1-4T). *=significantly different from 30 Hz.

Figure 21:
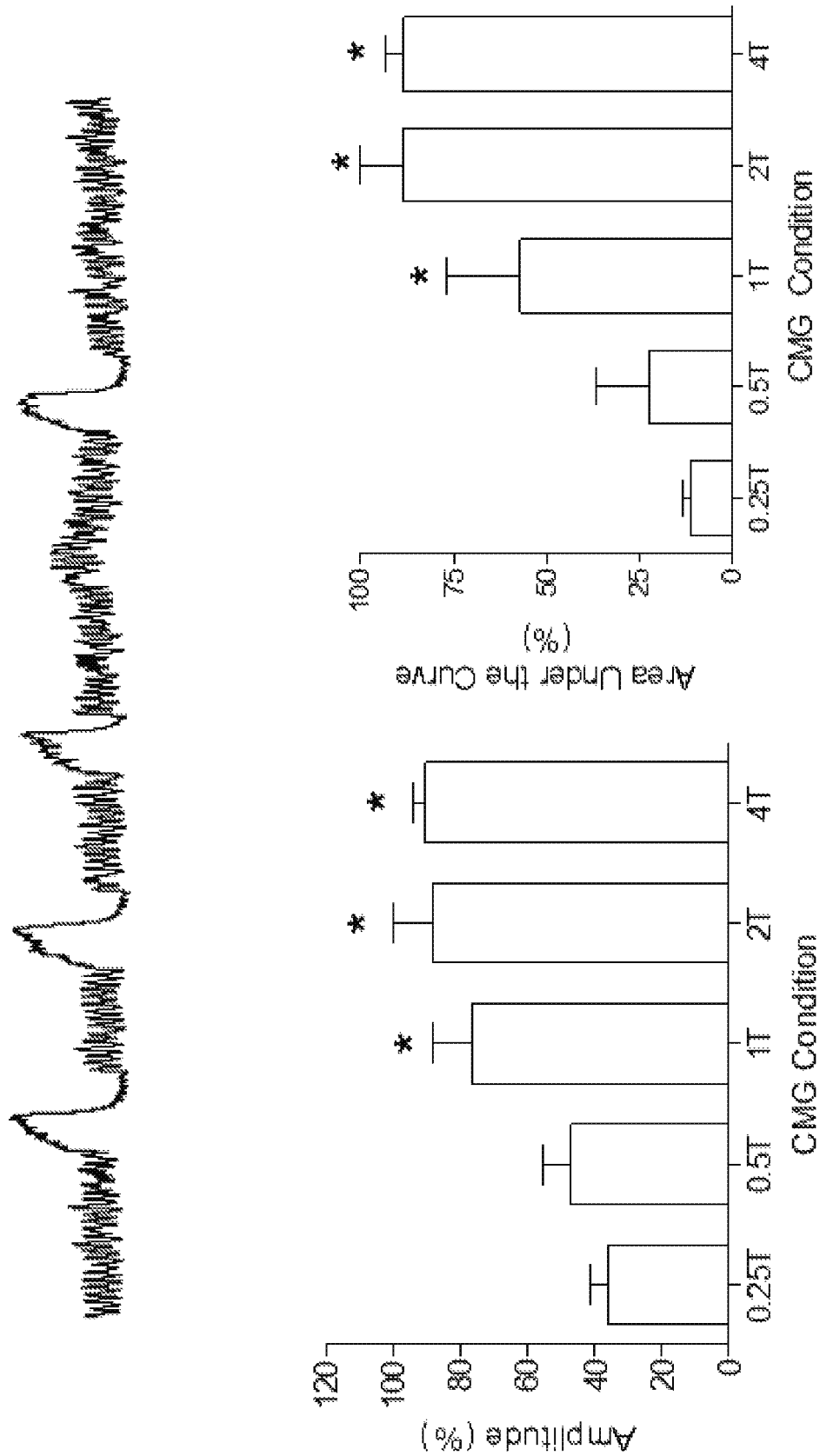

FIG. 21. Intensity responses of tibial nerve stimulation (TNS) when bladder is in retention. TNS (1 Hz, 0.2 ms, 1-4T). *=significantly different from 0.25T.

Figure 22:
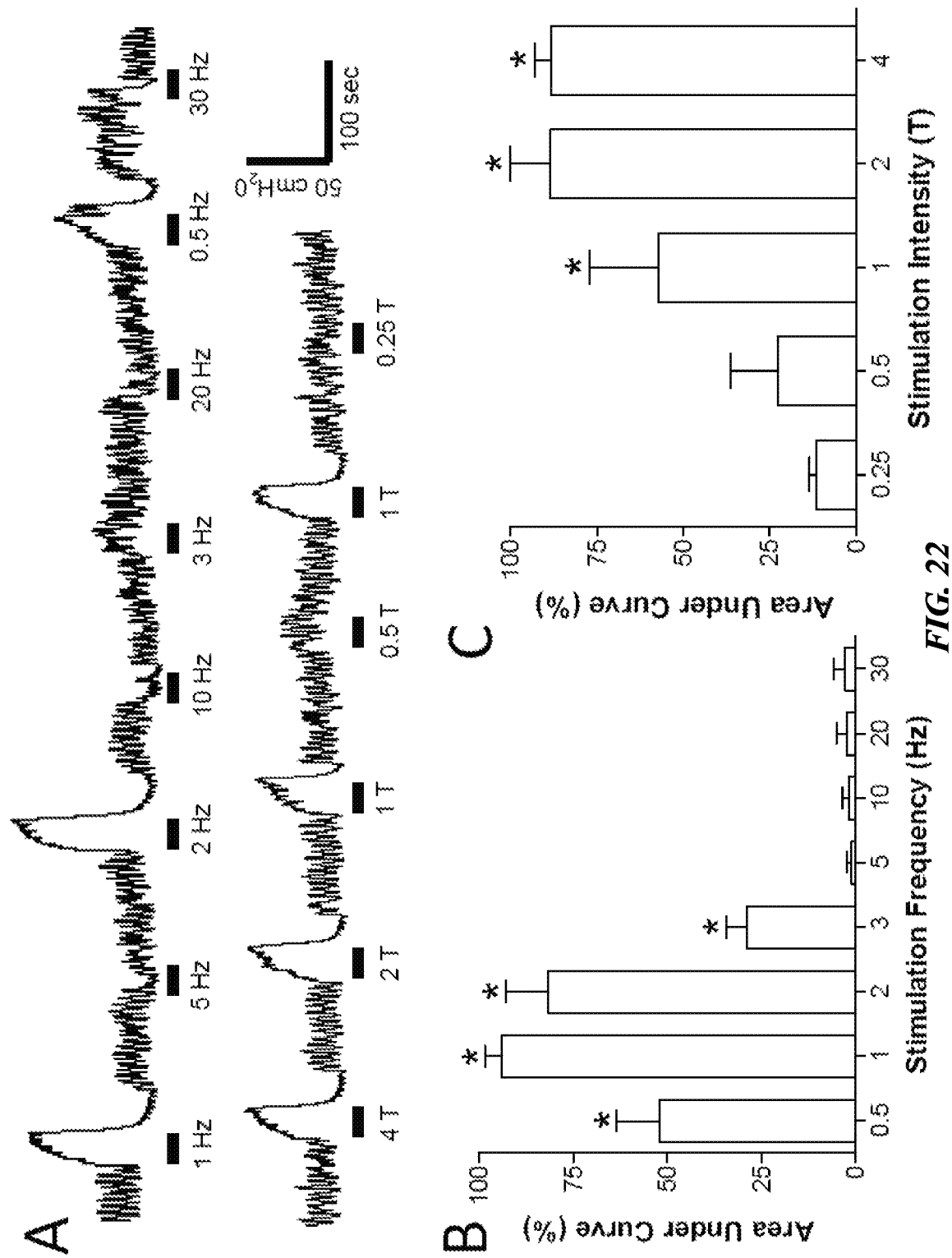

FIG. 22. Bladder pressure responses to different frequencies (0.5-30 Hz) and intensities (0.25-4T) of tibial nerve stimulation (TNS). T±threshold intensity for TNS to induce toe twitch. A: bladder pressure traces from the same cat. The black bar under the pressure trace indicates the duration (30 secs) of TNS. TNS: 4T=6.4 V, 0.2 ms for top trace; 1 Hz, 0.2 ms for bottom trace. B: Normalized area under curve for different frequencies of TNS (4T=1.6-6.4 V, 0.2 ms). C: Normalized area under curve for different intensities of TNS (1 Hz, 0.2 ms). * significantly ($p<0.05$) different from the response at 30 Hz in B or at 0.25T in C (one-way ANOVA). N=4 cats.

Figure 23:
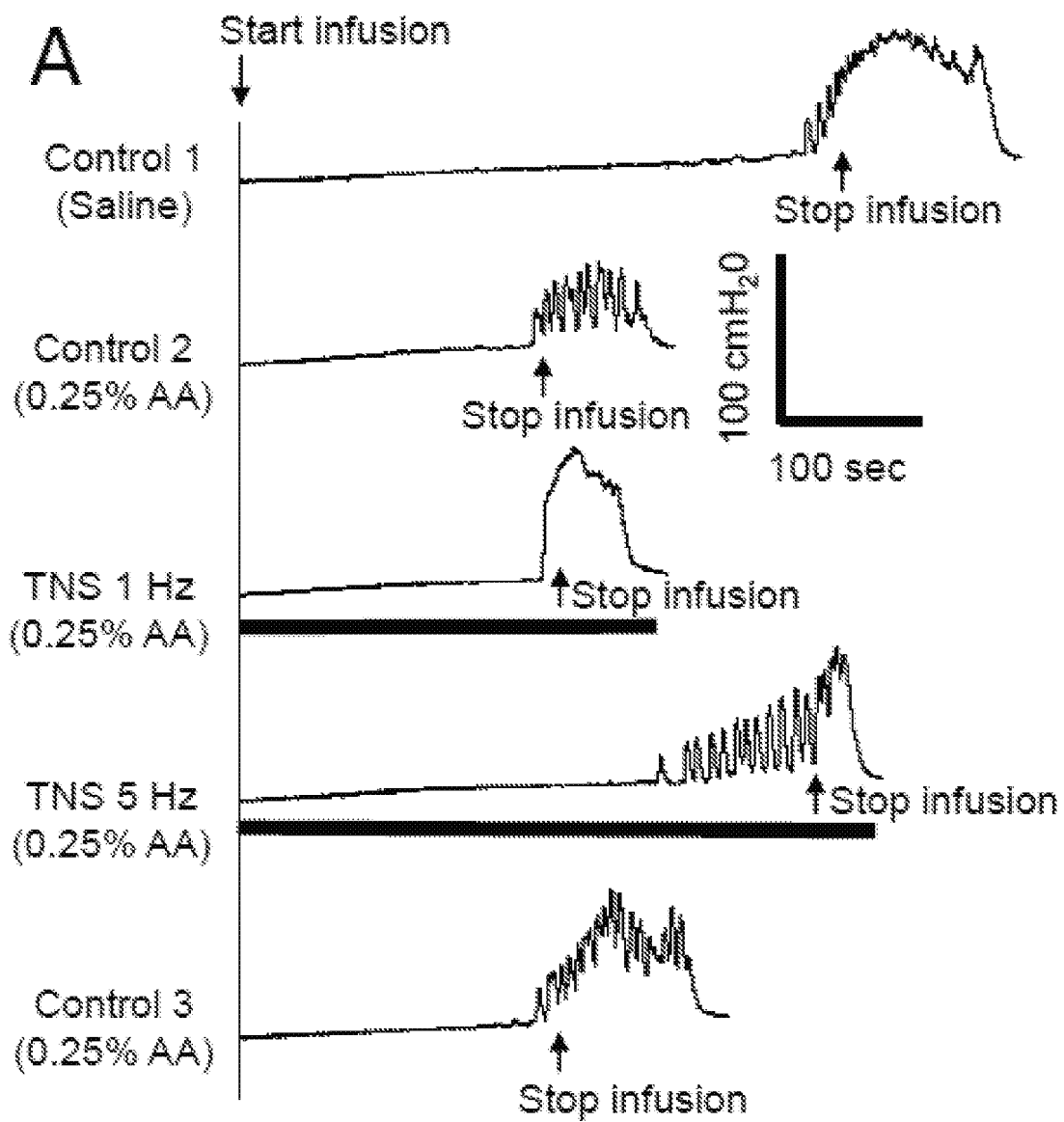

FIG. 23. Effects of 1 Hz and 5 Hz tibial nerve stimulation (TNS) on bladder overactivity induced by acetic acid (AA) irritation. Intravesical infusion of dilute (0.25%) AA irritated the bladder and caused bladder overactivity resulting in a smaller bladder capacity. TNS at 1 Hz did not change the small bladder capacity, but at 5 Hz increased the bladder capacity. 1 Hz and 5 Hz TNS: 4T=2.4 V, 0.2 ms. Infusion rate=2 ml/min.

Figure 24:
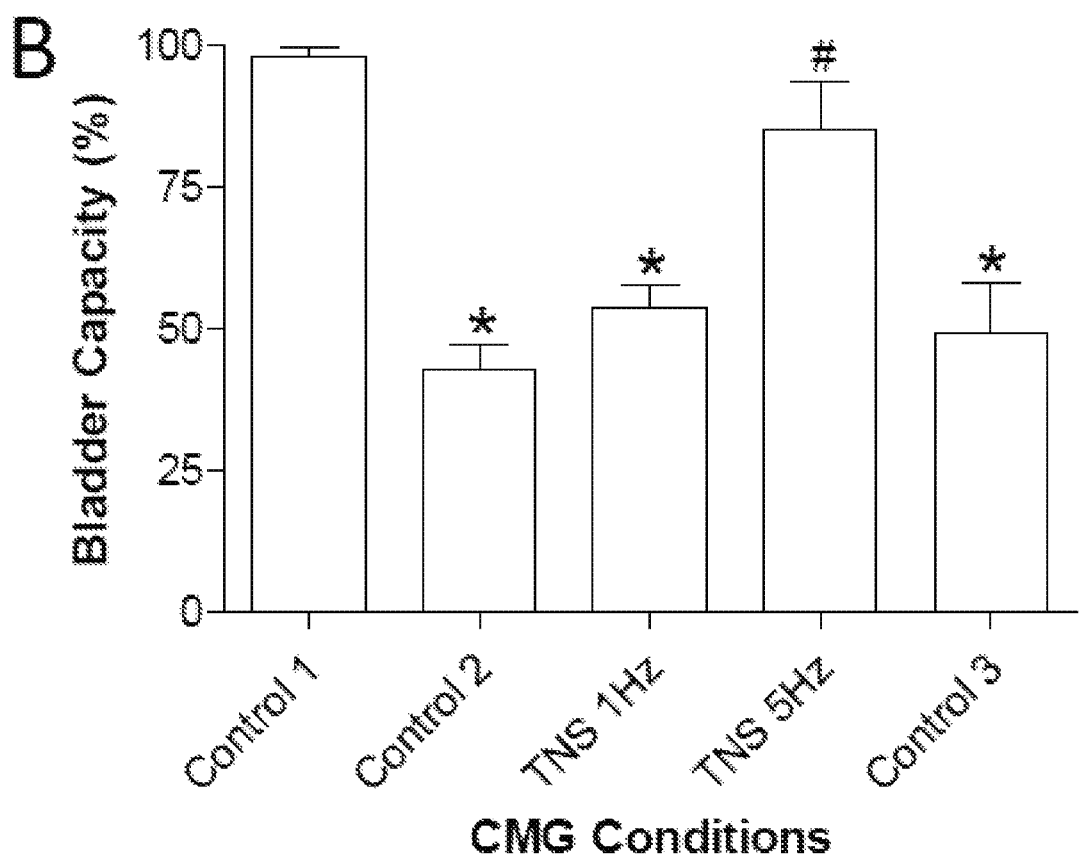

FIG. 24. Effects of 1 Hz and 5 Hz tibial nerve stimulation (TNS) on bladder overactivity induced by acetic acid (AA) irritation. Summarized results from 6 cats. 1 Hz TNS: 4T=1.6-8 V, 0.2 ms. 5 Hz TNS: 4T=0.8-2.4 V, 0.2 ms. * significant ($p<0.05$) different from control 1 (one-way ANOVA). # significantly different from ($p<0.05$) control 2 (one-way ANOVA).

Figure 25:
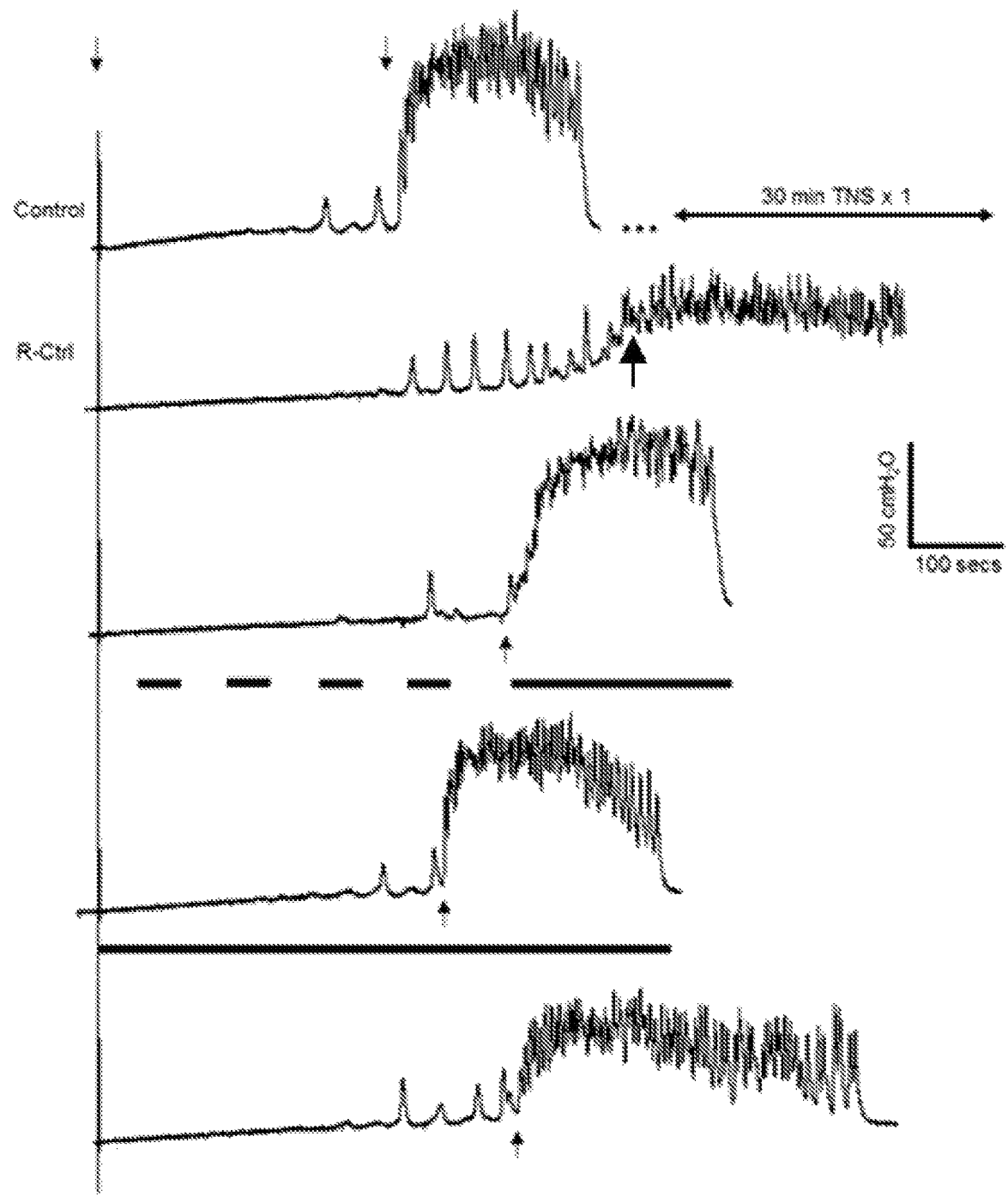

FIG. 25. Effect of sural nerve stimulation (SUR) on bladder capacity in retention state. Repeated CMG tracings with intermittent and continuous SUR. The arrowed line indicates tibial nerve stimulation (TNS×1, 30 min, 6T=3 V, 0.5 Hz, 0.2 ms). The black bar under the bladder pressure tracing indicates the duration of SUR (1 Hz, 0.2 ms, 80 V). T—threshold intensity to induce observable muscle twitch at the back thigh.

Figure 26:
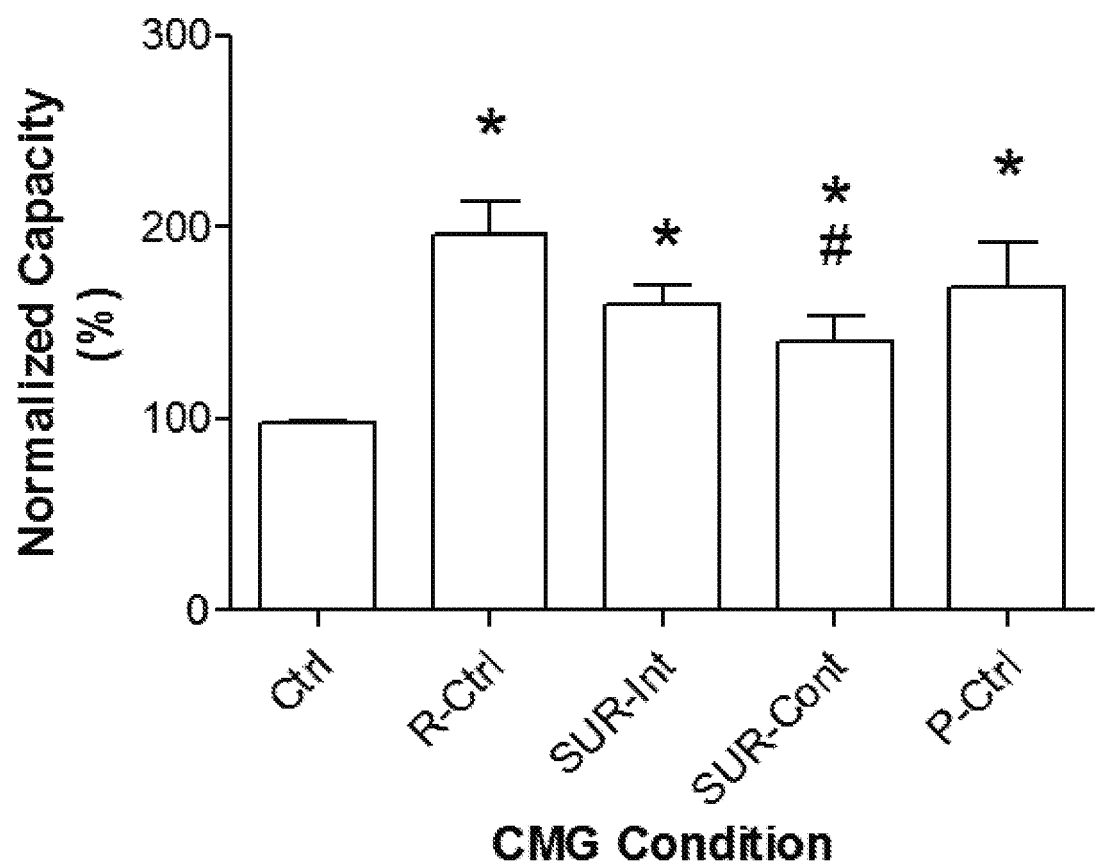

FIG. 26. Effect of sural nerve stimulation (SUR) on bladder capacity in retention state. Summarized results (N=6 cats). Bladder capacity was normalized to the control capacity. * significantly ($p<0.01$) different from the control capacity (one-way ANOVA). # significantly ($p<0.01$) different from the retention control (R-ctrl) capacity (one-way ANOVA). SUR (1-2 Hz, 0.2 ms, 10-80 V). TNS (×1-5 for 30 min, 5 Hz, 0.2 ms, 4-6T–1.6 V-40 V).

Figure 27:
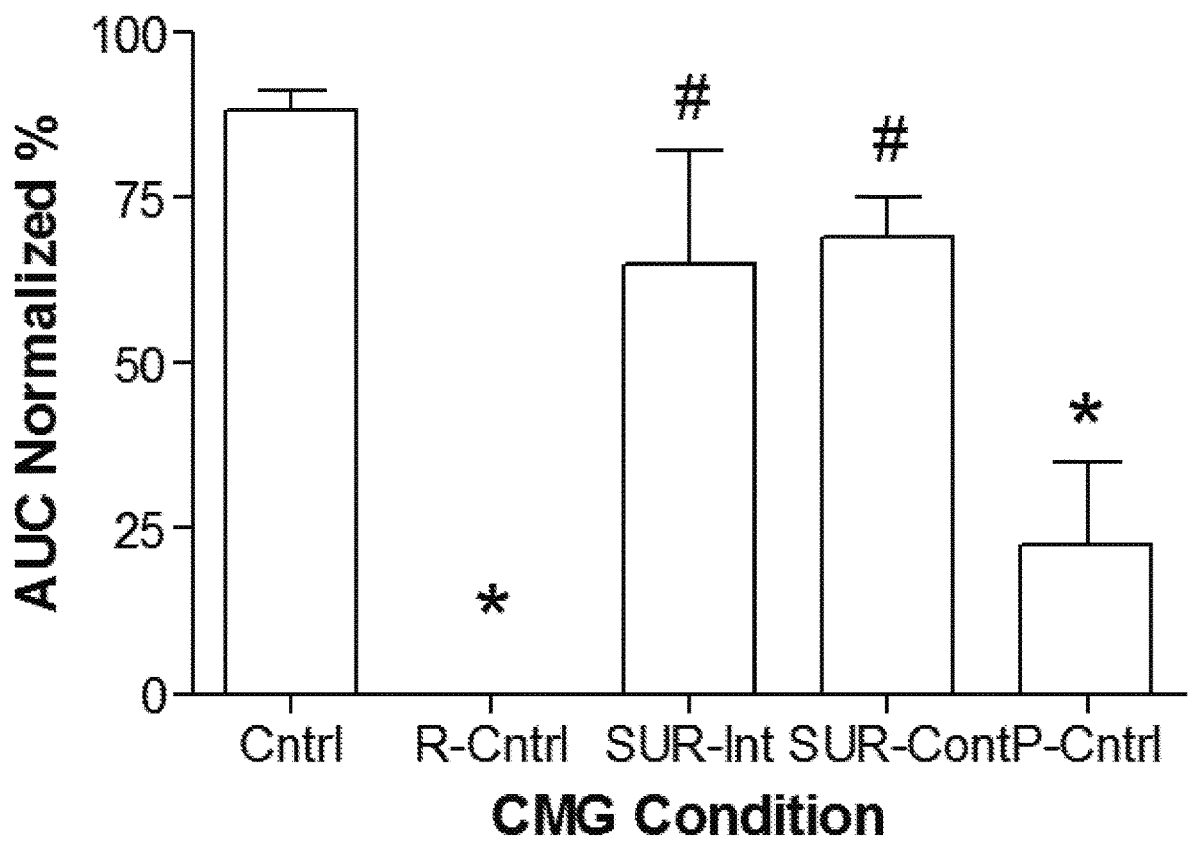

FIG. 27. Effects of sural nerve stimulation (SUR) on bladder contraction under retention conditions (N=6). Area under the curve of bladder contraction pressure. * significantly ($p<0.01$) different from the control capacity (one-way ANOVA). # significantly ($p<0.01$) different from the retention control (R-ctrl) capacity (one-way ANOVA). SUR (1-2 Hz, 0.2 ms, 10-80 V). TNS (×1-5 for 30 min, 1-5 Hz, 0.2 ms, 4-6T=1.6 V-40 V).

Figure 28:
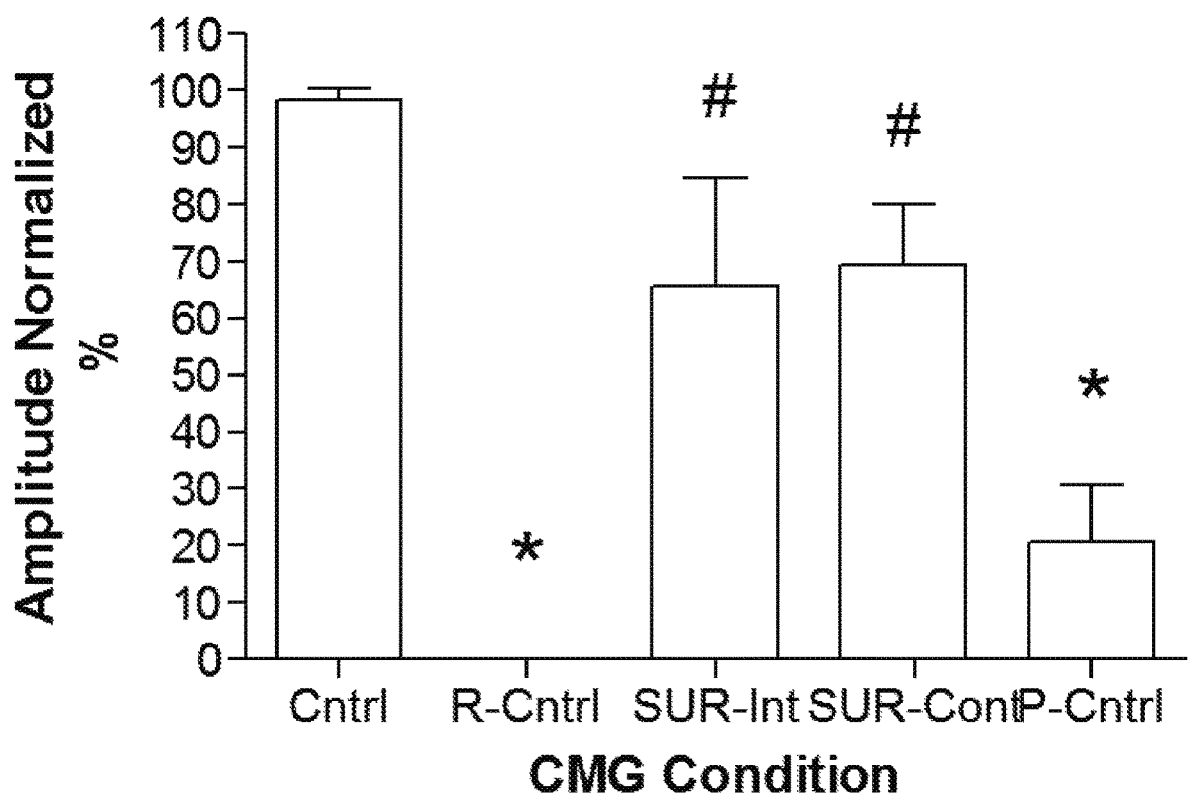

FIG. 28. Effects of sural nerve stimulation (SUR) on bladder contraction under retention conditions (N=6). Contraction amplitude. * significantly ($p<0.01$) different from the control capacity (one-way ANOVA). # significantly ($p<0.01$) different from the retention control (R-ctrl) capacity (one-way ANOVA). SUR (1-2 Hz, 0.2 ms, 10-80 V). TNS (×1-5 for 30 min, 1-5 Hz, 0.2 ms, 4-6T=1.6 V-40 V).

Figure 29:
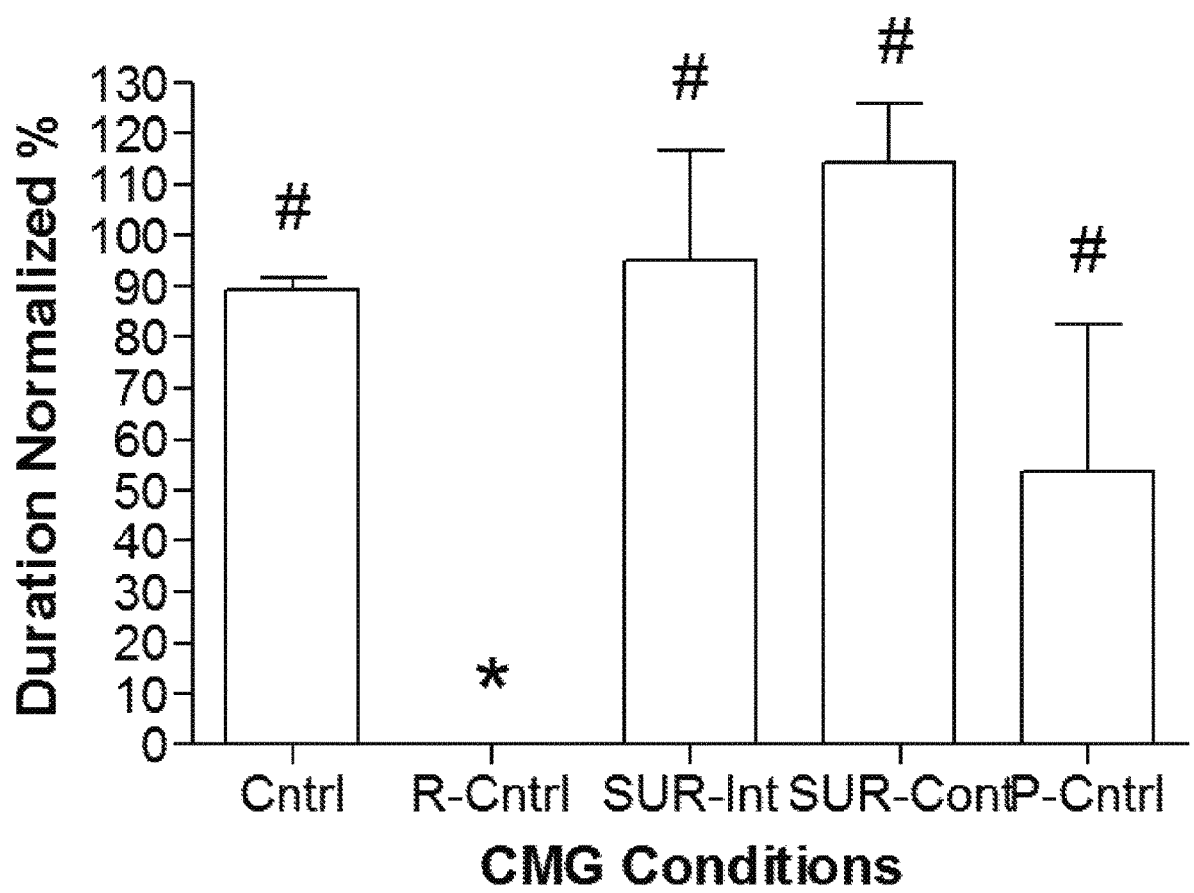

FIG. 29. Effects of sural nerve stimulation (SUR) on bladder contraction under retention conditions (N=6). Contraction during bladder contraction response normalized to control capacity. * significantly ($p<0.01$) different from the control capacity (one-way ANOVA). # significantly ($p<0.01$) different from the retention control (R-ctrl) capacity (one-way ANOVA). SUR (1-2 Hz, 0.2 ms, 10-80 V). TNS (×1-5 for 30 min, 1-5 Hz, 0.2 ms, 4-6T=1.6 V-40 V).

Figure 30:
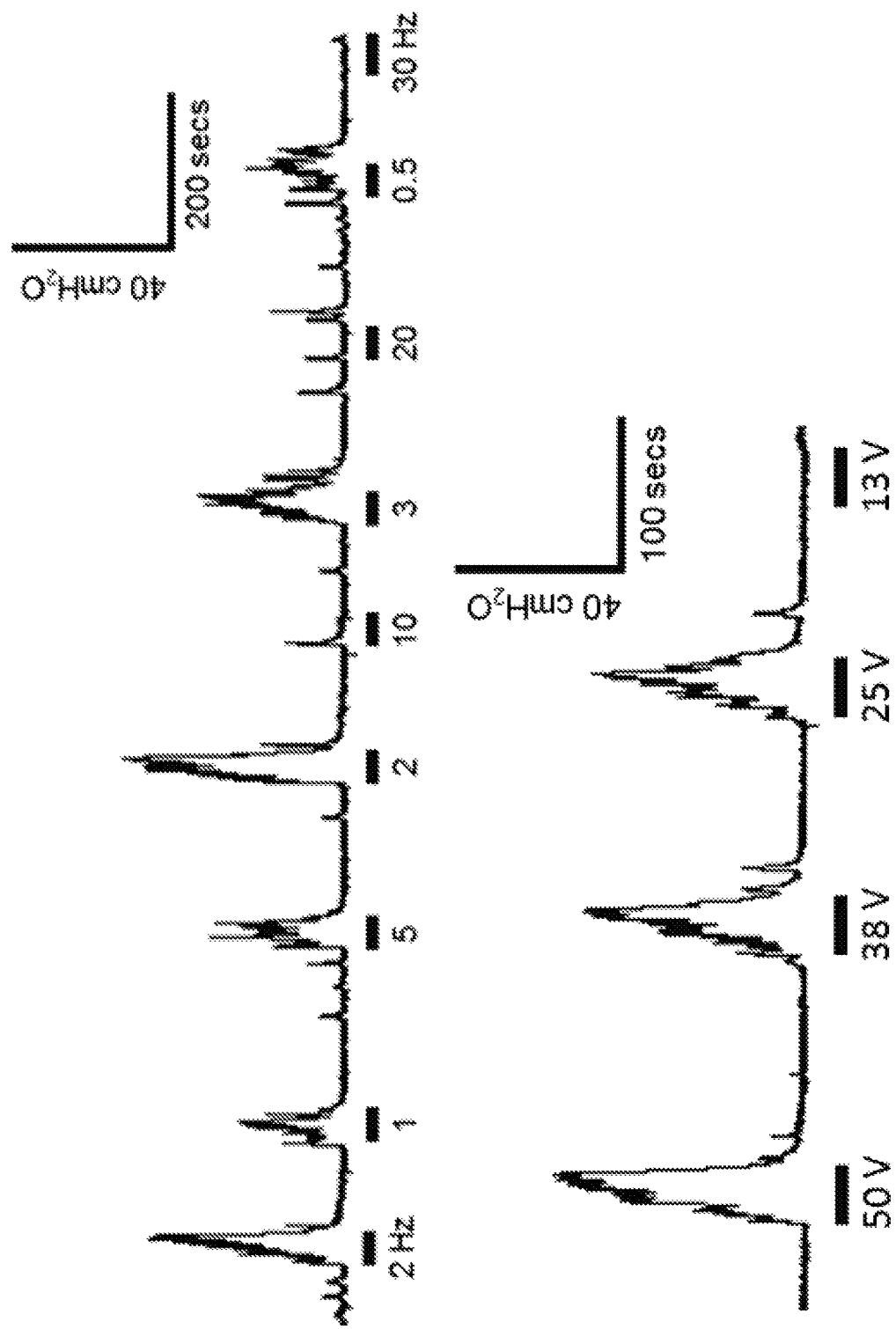

FIG. 30. Bladder pressure responses to different frequencies (0.5-30 Hz) and intensities (13-50 V) of sural nerve stimulation (SUR) under retention conditions. (Top) Bladder pressure tracings. The black bar under the pressure tracing indicates the duration (30 secs) of SUR (0.2 ms, 50 V). (Bottom) Bladder pressure responses to different frequencies (0.5-30 Hz) and intensities (13-50 V) of sural nerve stimulation (SUR) under retention conditions. Bladder pressure tracings. The black bar under the pressure tracing indicates the duration (30 secs) of SUR (0.2, 2 Hz)

Figure 31:
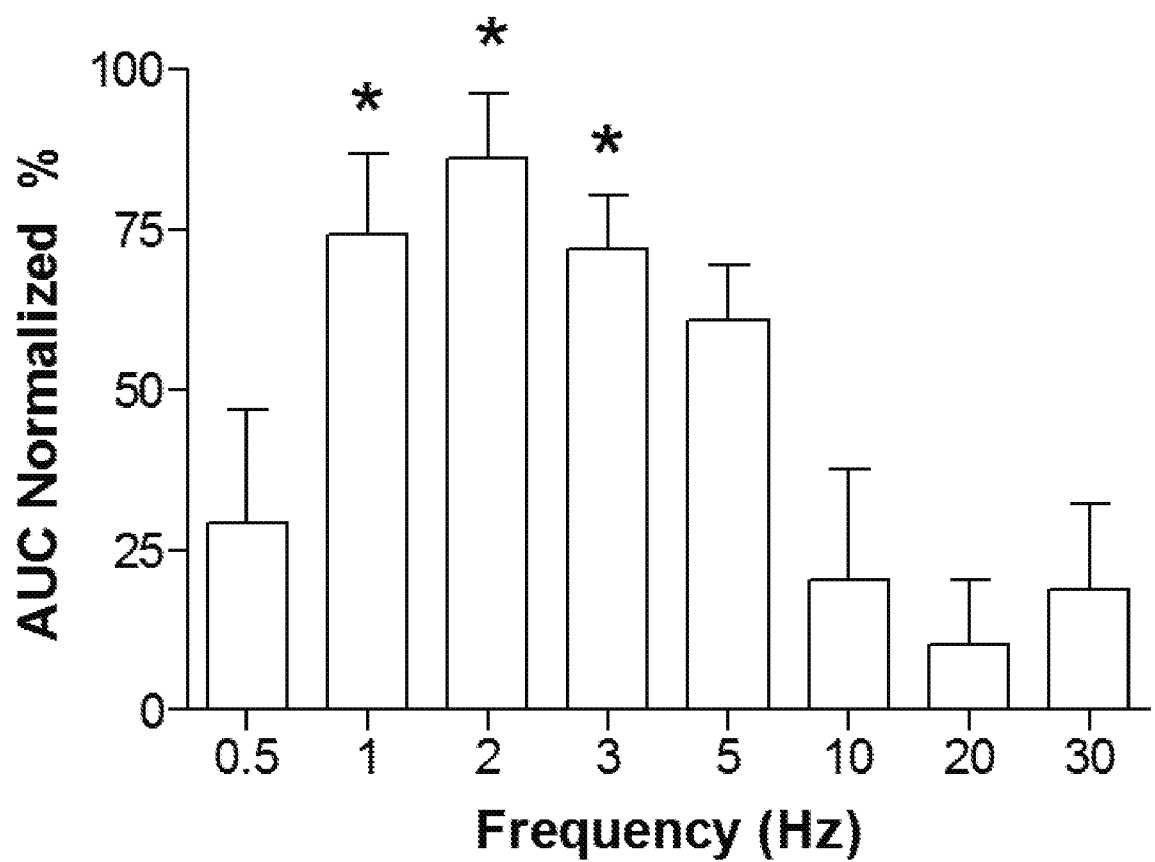

FIG. 31. Bladder pressure responses to different frequencies (0.5-30 Hz) and intensities (13-50 V) of sural nerve stimulation (SUR) under retention conditions. Normalized area under curve. Pressure response was normalized to the maximal response in each animal (N=5 cats). * significantly ($p<0.01$) different from the response at 30 Hz (one-way ANOVA).

Figure 32:
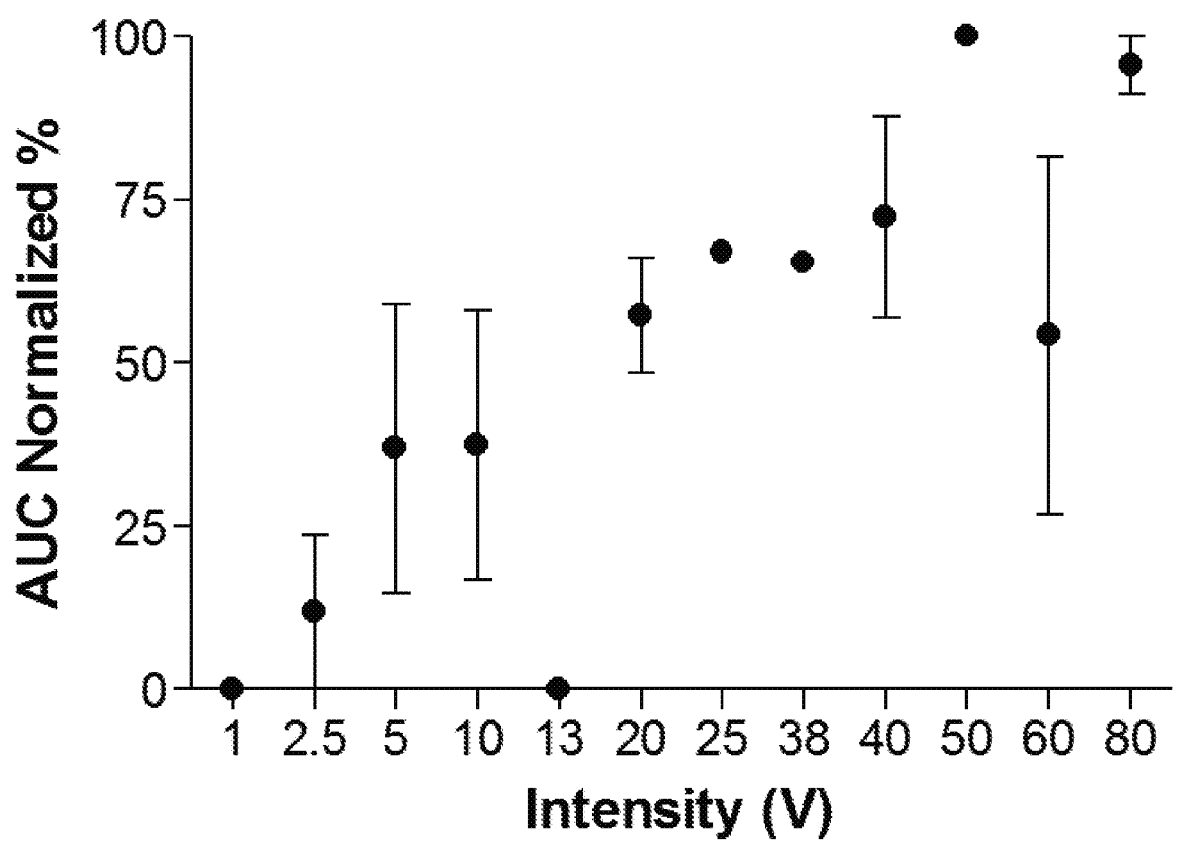

FIG. 32. Bladder pressure responses to different frequencies (0.5-30 Hz) and intensities (13-50 V) of sural nerve stimulation (SUR) under retention conditions. Scatter plot of normalized area under the curve at tested intensity.

DESCRIPTION OF THE INVENTION

The following description is merely exemplary in nature and is in no way intended to limit the invention, its application, or uses. While the description is designed to permit one of ordinary skill in the art to make and use the invention, and specific examples are provided to that end, they should in no way be considered limiting. It will be apparent to one of ordinary skill in the art that various modifications to the following will fall within the scope of the appended claims. The present invention should not be considered limited to the presently disclosed aspects, whether provided in the examples or elsewhere herein.

The use of numerical values in the various ranges specified in this application, unless expressly indicated otherwise, are stated as approximations as though the minimum and maximum values within the stated ranges are both preceded by the word "about". In this manner, slight variations above and below the stated ranges can be used to achieve substantially the same results as values within the ranges. Also, unless indicated otherwise, the disclosure of ranges is intended as a continuous range including every value between the minimum and maximum values. As used herein "a" and "an" refer to one or more.

As used herein, the electrodes and base are described as overlaying an anatomical feature. This means that the described electrodes or base are positioned or configured/adapted for placement on skin superficial to (overlaying) a specific anatomical feature, such as an area of the foot, nerves, and/or the bone(s) underlying the skin at that area of the foot. That is, the specified bone lies partially or wholly underneath the skin said to be overlaying the specified bone and/or nerve. Skin overlaying a specified bone can overlap the specified bone and another bone. To facilitate description of the position of an electrode in the foot, the "anterior-to-posterior axis" of the foot is an axis extending from the toes (anterior) to the heel (posterior) in an anterior to posterior direction. Likewise, "medial," "lateral," "dorsal," "plantar," "superficial," "proximal" and "distal" have their art-recognized meanings.

Figure 1:
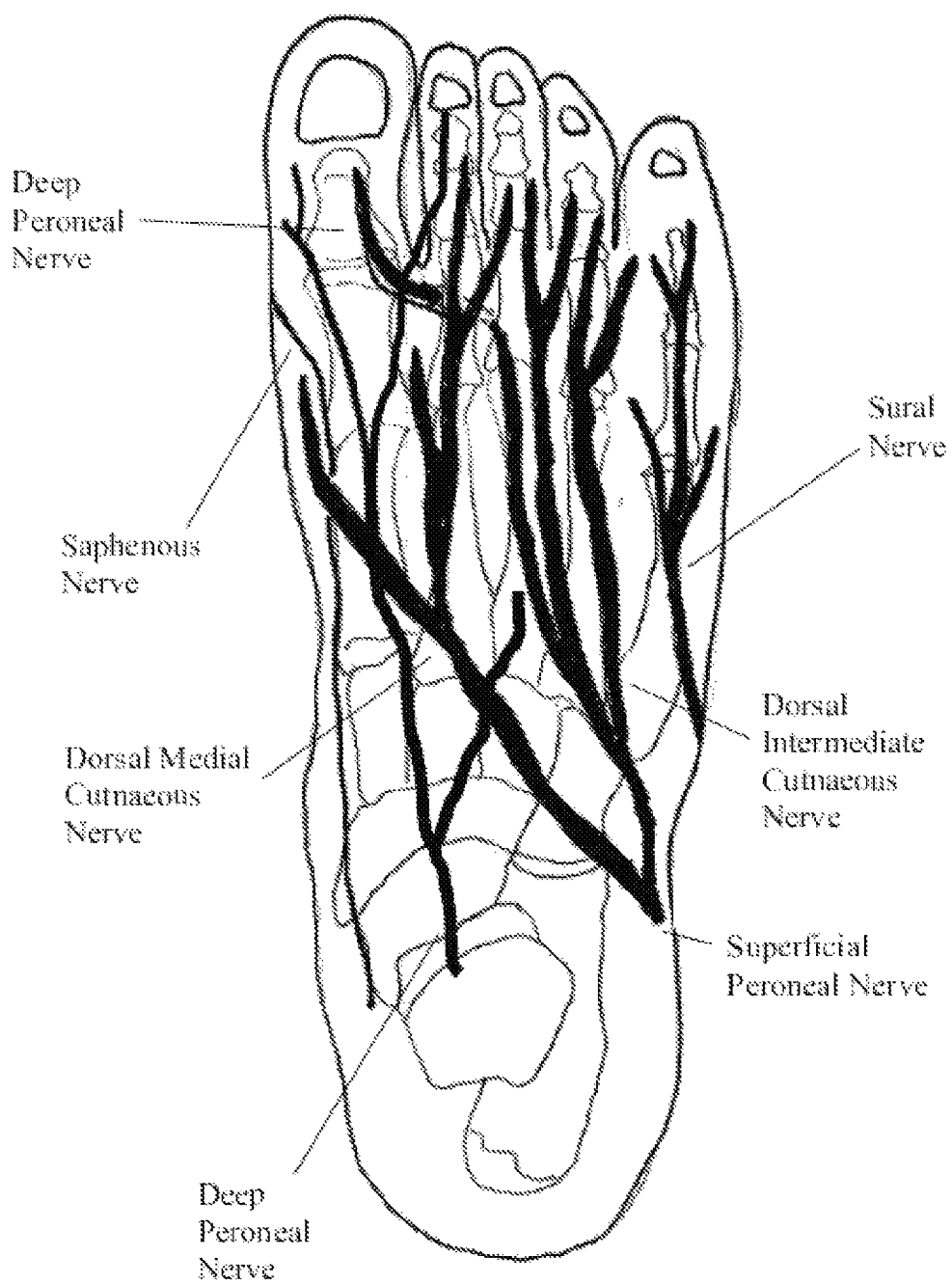
FIG. 1. A schematic diagram of the dorsal (top) surface of a human foot, showing the bones of the human foot and the nerves, including the superficial peroneal nerve, dorsal intermediate cutaneous nerve, dorsal medial cutaneous nerve, deep peroneal nerve, sural nerve, and saphenous nerve.

As used herein, the term "dorsal surface of the foot" refers to the top surface of the foot, including the ankle (talocrural) region and talocrural joint. FIG. 1 shows a view of the dorsal surface of the foot, including certain nerves.

As used herein, the term "plantar surface of the foot" refers to the sole, or bottom surface of the foot.

As used herein, the term "forefoot" refers to the part of the foot (both dorsal and plantar surface) including and superficial to the metatarsals and proximal phalanges of the foot. This is the widest (medial to lateral) section of the foot. The medial longitudinal arch is the medial arch of the foot, and includes the calcaneus, talus, navicular, cuneiform and the first through third metatarsal. Its posterior portion includes the calcaneus and talus bones, and the medial and lateral plantar nerves enter the sole of the foot from the ankle at this point.

As used herein, the term "midfoot" refers to the part of the foot (both dorsal and plantar surface) including and superficial to the cuboid, navicular, and/or cuneiform bones.

As used herein, the term "hindfoot" refers to part of the foot (both dorsal and plantar surface) including and superficial to the talus and/or calcaneus bones, and/or the talocrural joint.

As used herein, the term "predominance" means more than 50%, for example when it is stated that an electrode of the electrode-containing device described herein overlays a predominance of the superficial peroneal nerve and branches thereof, for example of the dorsal intermediate and dorsal medial cutaneous nerves or the lateral and medial plantar nerves in the forefoot, the electrodes cover an amount of skin on the dorsal or plantar surface of the foot that overlays at least 50% of the superficial peroneal or lateral and medial plantar nerves and branches thereof (e.g., with regard to the peroneal nerve, the dorsal intermediate and dorsal medial cutaneous nerves), deep peroneal nerve, sural nerve, and saphenous nerve at a given position in the anterior to posterior axis of the foot (e.g., on a frontal (coronal) plane) of the forefoot.

The ranges provided herein, for example and without limitation electric pulse frequencies, are based on experimentation on cats. The frequencies necessary to elicit a desired response in humans and cats are very similar. As illustrated in U.S. Pat. No. 7,047,078, stimulation of the pudendal nerve in human subjects produce similar results as compared to the results in cats. As such, frequency ranges applicable to cats are considered to be effective in human.

It should also be recognized that the optimal electrical stimulation parameters to elicit a desired effect may vary to some degree from subject-to-subject, depending on a number of factors. Optimal frequencies to elicit the desired goals can be adjusted from person-to-person. A "patient" may be human or animal and unless specified otherwise embraces a specific patient, a class of patients or any human or animal in a generic sense and does not imply any doctor-patient relationship. Thus, a structure configured to, or adapted to, a patient's foot includes structures configured to a specific patient and/or a group of patients.

Subject to the limitations presented herein, any positioning of electrodes on the leg or at the ankle (overlaying the superficial peroneal nerve, deep peroneal nerve, the tibial nerve, saphenous nerve, sural nerve, and/or the femoral cutaneous nerve) or on the foot (below the ankle (talocrural) joint of a patient, on the dorsal (top) surface of a foot to stimulate the sural, superficial peroneal, deep peroneal, or saphenous nerves, or on the plantar (bottom) surface of a foot to stimulate the medial plantar nerve and/or lateral plantar nerve) that is useful in modulating urological, bladder, urethral sphincter (internal and external), gastrointestinal, bowel, anal sphincter, and/or rectal contractions/activity should be considered within the scope of the present methods, and slight alterations of the specific positioning described below should also be considered to be within the scope of the described devices, systems, and methods. In addition, listing of a specific nerve should be understood to include branches of the nerve. That is, for example and without limitation, when it is stated that the superficial peroneal nerve is stimulated, such stimulation can include one or more branches of the superficial peroneal nerve.

Figure 2:
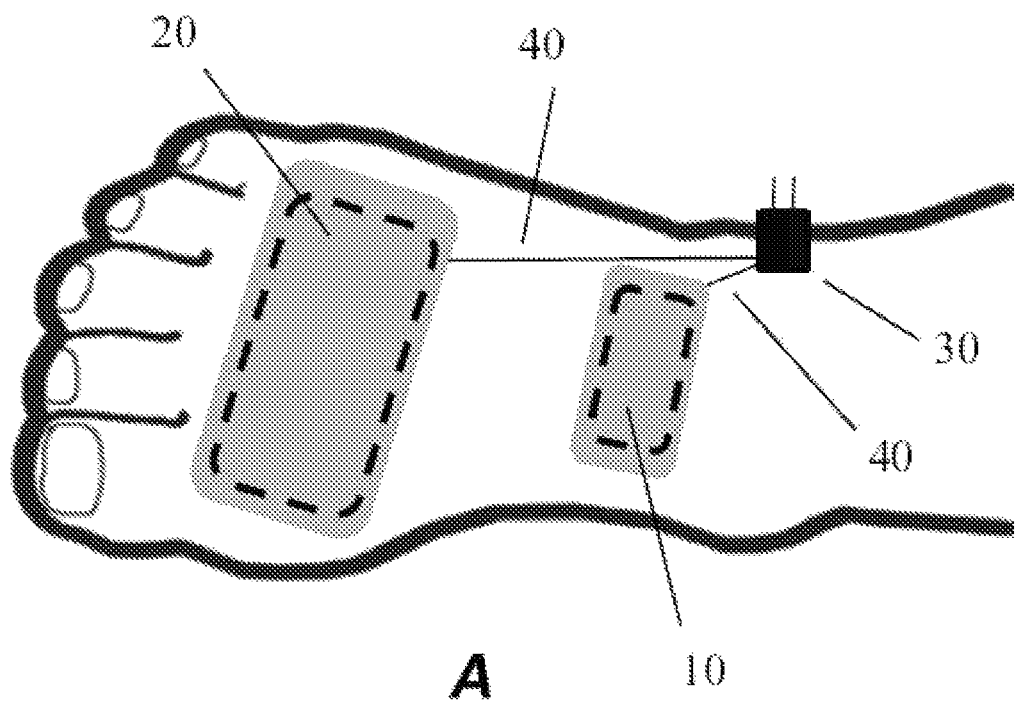
FIG. 2. Schematic diagrams of electrode placement on the dorsal (top panel) and plantar (bottom panel) surfaces of the foot according to one aspect of the methods described herein.
Figure 2:
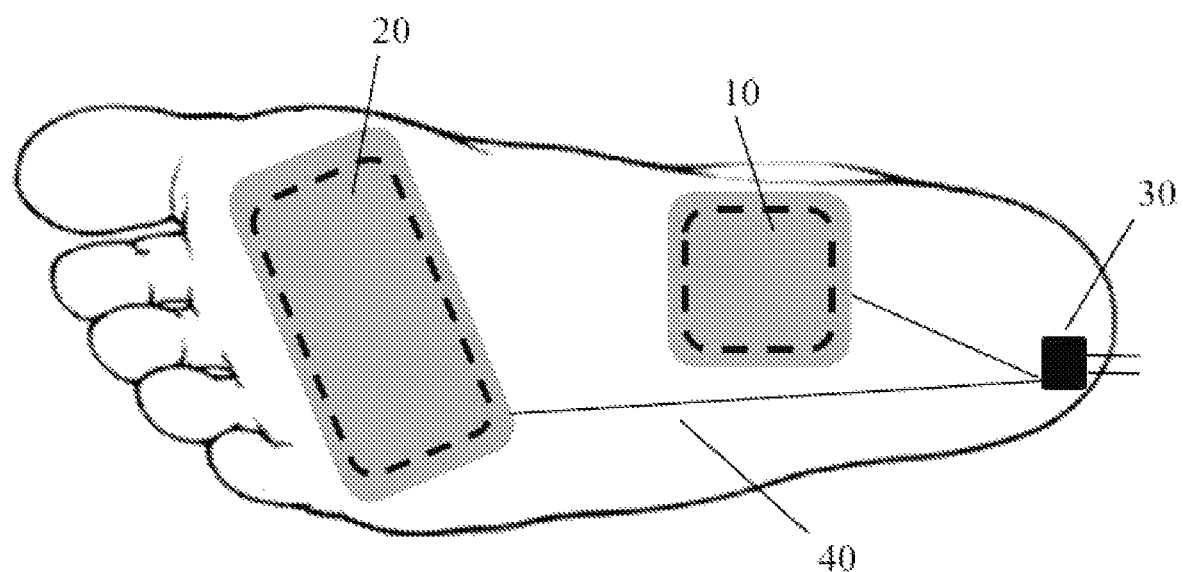

Provided herein are methods of treating UAB, urinary retention, detrusor-sphincter dyssynergia after spinal cord injury, constipation, and/or infrequent bowel movements through electrical stimulation of peripheral nerves. In aspects the stimulation is transcutaneous electrical stimulation through a first and second electrode. The first electrode can be a cathodal electrode and the second electrode can be an anodal electrode, or vice versa. Suitable devices for delivering such transcutaneous stimulation are disclosed in, for example and without limitation, U.S. Patent Publication No. 2013/0006322 and PCT Publication No. WO 2016/106182, each of which is incorporated herein by reference in their entirety. Suitable devices/systems are shown in FIG. 2. Specifically, those figures show first electrode (10), second electrode (20), a connector for a pulse generator (for example, and without limitation, those disclosed in U.S. Pat. Nos. 5,273,033; 3,881,494; and 3,902,502) (30), and wires or leads (40) for delivering current to the electrodes attached to the dorsal (top panel) or plantar (bottom panel) surface of the foot. It should be noted that these images are merely exemplary, and that a number of devices or systems can be used to deliver transcutaneous electrical stimulation, so long as the proper stimulation parameters described herein are utilized.

Specifically, stimulation for treating UAB and/or urinary retention includes pulses having a pulsewidth (duration) of 0.01 to 3 ms (all ranges therebetween inclusive), delivered at a frequency of between about 0.5 and about 3 Hz (all ranges therebetween inclusive), and having a strength of less than 5T (for example, between 1T and 4T, all ranges therebetween inclusive), where T is the threshold intensity at which a toe-twitch or muscle twitch in the leg is evoked and, in terms of voltage, typically falls within the range of about 1 to about 20 V, such as about 3 to about 16 V, all ranges therebetween inclusive. Without wishing to be bound by the theory, 5T is believed to be the approximate threshold at which pain is experienced with electrical stimulation. The present methods provide relief from the symptoms of UAB and/or urinary retention without concomitant pain from stimulation that is too intense (e.g., 5T or greater), and thus are superior to other methods. Concomitant pain from the stimulation prevents clinical application of the stimulation.

In aspects, the pulses are delivered with a pulsewidth of about 0.2 ms, at a frequency of about 1 to about 2 Hz, and having a strength of about 1T to about 2T. In some aspects, the pulses are delivered with a pulsewidth of 0.2 ms, at a frequency of 1 Hz, with a strength of 1T. In some aspects, the pulses are delivered with a pulsewidth of 0.2 ms, at a frequency of 2 Hz, with a strength of 1T. In some aspects, the pulses are delivered with a pulsewidth of 0.2 ms, at a frequency of 1 Hz, with a strength of 2T. In some aspects, the pulses are delivered with a pulsewidth of 0.2 ms, at a frequency of 2 Hz, with a strength of 2T. In some aspects, the pulses are delivered with a pulsewidth of 0.2 ms, at a frequency of 3 Hz, with a strength of 1T. In some aspects, the pulses are delivered with a pulsewidth of 0.2 ms, at a frequency of 3 Hz, with a strength of 2T. Those of ordinary skill in the art will appreciate that anatomy and physiology for a given patient can vary the effective stimulation parameters slightly.

Stimulation can be delivered as needed, for a duration suitable to provide relief from symptoms of UAB and/or urinary retention. For example, and without limitation, in aspects of the method, the patient's nerve is stimulated for from 0.1 to 60 minutes (all ranges therebetween inclusive). In some aspects, the patient's nerve is stimulated for at least 30 seconds. In some aspects, the patient's nerve is stimulated continuously, 24 hours and 7 days. In some aspects, the patient's nerve is stimulated during the entire voiding period lasting about 1-5 minutes. In some aspects, the patient's nerve is stimulated for a period of time, followed by a period of equal or different duration where no stimulation is applied, and the cycle is repeated one or more times, for example 5 times, 10 time, 20 times, or more.

The waveform of the pulses may vary, so long as the desired effect is realized. Examples of suitable waveforms include sine, square, rectangular, triangle sawtooth, rectilinear, pulse, exponential, truncated exponential, and damped sinusoidal. One skilled in the art will appreciate that other types of electrical stimulation may also be used in accordance with device, system and methods described herein. Monophasic or biphasic stimuli, or a mixture thereof may be used. Damage to nerves by the application of an electrical current may be minimized, as is known in the art, by application of biphasic pulses or biphasic waveforms to the nerve(s), as opposed to a monophasic pulses or waveforms that can damage nerves in some instances of long-term use. "Biphasic current," "biphasic pulses" or "biphasic waveforms" refer to two or more pulses that are of opposite polarity that typically are of equal or substantially equal net charge (hence, biphasic and charge balanced) and may be symmetrical asymmetrical or substantially symmetrical. This is accomplished, for example, by applying, via an electrode, one or more positive pulses, followed by one or more negative pulses, typically of the same amplitude and duration as the positive pulses, or vice versa, such that the net charge applied to the target of the electrode is zero or approximately zero. The opposite polarity pulses may have different amplitudes, profiles or durations, so long as the net applied charge by the biphasic pulse pair (the combination of the positive and negative pulses) is approximately zero.

In aspects, UAB and/or urinary retention is treated using electrical stimulation having parameters as described herein applied to one or more nerves to evoke a physiological response. In aspects, UAB and/or urinary retention is treated using electrical stimulation having parameters as described herein applied to the superficial peroneal nerve through electrodes overlaying the dorsal surface of the foot of a patient. In aspects, UAB and/or urinary retention is treated using electrical stimulation having parameters as described herein applied to the deep peroneal nerve through electrodes overlaying the dorsal surface of the foot of a patient. In further aspects, UAB and/or urinary retention is treated using electrical stimulation having parameters as described herein applied to the medial plantar nerve and/or lateral plantar nerve through electrodes overlaying the plantar surface of the foot of a patient. In aspects, UAB and/or urinary retention is treated using electrical stimulation having parameters as described herein applied to the saphenous nerve through electrodes overlaying the dorsal surface of the foot of a patient. In further aspects, UAB and/or urinary retention is treated using electrical stimulation having parameters as described herein applied to the sural nerve through electrodes overlaying the dorsal surface of the foot or the ankle of a patient. In still further aspects, UAB and/or urinary retention is treated using electrical stimulation having parameters as described herein applied to the superficial peroneal nerve, deep peroneal nerve, tibial nerve, saphenous nerve, sural nerve, and/or femoral cutaneous nerve through electrodes overlaying the leg of a patient.

In aspects, treatment of UAB and/or urinary retention includes treatments that increase bladder sensation such as the first desire to void, the strong desire to void, urgency, or strong urgency. In aspects, methods that increase bladder sensation increase the sensation to a degree that enables a patient to initiate voiding at a small bladder volume that, typically in urinary retention, does not generate such sensation. Stimulation parameters as described herein are suitable for increasing bladder sensation.

In further aspects, treatment of UAB and/or urinary retention includes treatments that elicit voiding of the bladder. In aspects, the voiding includes a relaxation of the urethral sphincter (internal and external) and a simultaneous contraction of the bladder. In some aspects, the voiding that is elicited is low pressure voiding without forcing urine back to the kidney(s). Stimulation parameters as described herein are suitable for eliciting voiding.

In aspects, treatment of infrequent bowel movements can include treatments that increase bowel sensation. In aspects, methods that increase bowel sensation increase the sensation of defecation urgency to a degree that enables a patient to initiate defecation. Stimulation parameters as described herein are suitable for increasing bowel sensation.

In further aspects, treatment of infrequent bowel movements includes treatments that elicit defecation and/or treat constipation. Stimulation parameters as described herein are suitable for eliciting defecation and/or treating constipation.

The foot/leg stimulation methods described above, using devices and systems for delivering transcutaneous stimulation, are a type of neuromodulation that is less invasive and less troublesome to the user. The devices and systems send modulatory neural signal from the nerves of the foot/leg to the CNS. The following example shows that neuromodulation caused by delivering stimulation to the foot through at least one cathodal and at least one anodal electrode can modulate the CNS to stimulate the bladder. However, in aspects, invasive stimulation may be desired.

Accordingly, also provided herein are invasive methods of treating UAB, urinary retention, detrusor-sphincter dyssynergia after spinal cord injury, constipation, and/or infrequent bowel movements through electrical stimulation of peripheral nerves through electrodes surgically implanted on or near the nerves. Suitable devices for delivering such direct nerve stimulation are disclosed in, for example and without limitation, U.S. Pat. No. 9,623,243, which is incorporated herein by reference in its entirety.

Specifically, for example and without limitation, electrodes useful for the methods disclosed herein can be manufactured from stainless steel, platinum, or other suitable materials. The electrodes can be monopolar, bipolar, or tripolar electrodes, with or without a cuff wrapping, and can be attached directly to any of nerves disclosed herein through a surgical procedure. Useful pulse generators for the methods described herein need only have a single output channel for delivering stimulation, or multiple output channels to simultaneously stimulate multiple nerves. In aspects, however, a pulse generator can include multiple channels for simultaneous, near simultaneous, sequential, or random stimulation of more than one of the nerves described herein. A pulse generator can also be implanted, and can be a programmable pulse generator (i.e. a "smart" device) or can be a pulse generator that is pre-programmed to only deliver pulses with set parameters. With regard to such "smart" devices, the pulse generator can be controlled wirelessly, and can receive instructions from smart phones, tablets, desktop computers, laptop computers, and the like. Stimulation parameters as described herein can then be applied directly to the nerve to stimulate the desired physiological response. As with transcutaneous stimulation described herein above, implanted electrodes can be utilized to stimulate one or more of the superficial peroneal nerve, deep peroneal nerve, tibial nerve, saphenous nerve, sural nerve, and/or femoral cutaneous nerve.

As with transcutaneous stimulation, damage to nerves by the application of an electrical current may be minimized, as is known in the art, by application of biphasic pulses or biphasic waveforms to the nerve(s), as opposed to a monophasic pulses or waveforms that can damage nerves in some instances of long-term use.

Normal physiological bladder voiding requires a relaxation of the urethral sphincter (internal and external) and a simultaneous contraction of the bladder. Without urethral relaxation, voiding cannot occur, or voiding occurs with a high bladder pressure to overcome the urethral resistance. High pressure voiding is dangerous because the high pressure pushes the urine back to the kidney, causing kidney failure and death. Therefore, the methods described herein elicit a relaxation of the urethral sphincter and a simultaneous contraction of the bladder to generate a low pressure voiding. The methods described herein are fundamentally different from other methods that elicit only a bladder contraction or only a urethral sphincter relaxation. For example, bladder pressure/contraction can be easily elicited by manually pressuring on the abdomen, which will not relax the urethral sphincter. The methods described herein are superior to the manual pressing.

The following are non-limiting examples of the use of electrical stimulation of the foot to cause bladder contraction, and are exemplary only and are not intended to limit the scope of the inventions described herein in any way.

Example 1—Peroneal Nerve Stimulation

In the present experiments it was discovered that electrical stimulation of the superficial peroneal nerve, which innervates the dorsal surface of the foot, elicits excitatory effects on the bladder and reverses prolonged tibial nerve stimulation-induced inhibition of contractions (TNS). These observations raise the possibility that the excitatory peroneal-to-bladder reflex might be utilized in clinical applications to enhance bladder contractions and treat UAB or non-obstructive urinary retention (NOUR).

Materials and Methods

The experimental protocol and animal use in this study were approved by the Animal Care and Use Committee at the University of Pittsburgh.

A total of 10 cats (7 male and 3 female, 2.9-4.2 kg; Liberty Research, Waverly, N.Y.) were used in this study. The animals were anesthetized with isoflurane (2-5% in oxygen) during surgery and then switched to α-chloralose anesthesia (initial 65 mg/kg i.v. and supplemented as needed) during data collection. Left cephalic vein was catheterized for administration of anesthetics and fluid. A tracheotomy was performed and a tube was inserted to keep the airway patent. A catheter was inserted into right carotid artery to monitor systemic blood pressure. Heart rate and blood oxygen were monitored by a pulse oximeter (9847V; NONIN Medical, Plymouth, Minn.) attached to the tongue. Through an abdominal incision, the ureters were isolated, tied, and cut for external drainage. A double lumen catheter was inserted into the bladder via a small cut in the proximal urethra and secured by a ligature around the urethra. One lumen was connected to a pump to slowly (1-3 ml/min) infuse saline to induce bladder distention. The other lumen was attached to a pressure transducer to measure bladder pressure. The superficial peroneal nerve and tibial nerve on the right side were dissected via skin incisions at the ankle for implantation of tripolar cuff electrodes (NC223pt, MicroProbe, Gaithersburg, Md.). The cuff electrodes were then connected to a dual channel electrical stimulator (S88; Grass Medical Instruments, Quincy, Mass.) via constant voltage stimulus isolators (SIU5; Grass Medical Instruments). After the surgery, the skin and muscle layers were closed by sutures. In 3 cats, the dorsal surface of left foot was shaved to fully remove the fur using depilatory cream, so that adhesive skin surface electrodes (1 cm diameter) could be attached to the foot for transcutaneous stimulation of the branches of the superficial peroneal nerve (FIG. 9, panel B).

At the beginning of each experiment, uniphasic rectangular pulses (1 Hz frequency) were used to determine the intensity threshold (T) for superficial peroneal nerve stimulation (PNS) to induce observable muscle twitches on the posterior thigh. The twitches disappeared when PNS frequency was increased above 2 Hz. Based on previous studies, the intensity threshold (T) for TNS to induce observable toe twitch was determined by uniphasic rectangular pulses at 5 Hz frequency. Pulse width of 0.2 ms was used for both PNS and TNS.

Initially, multiple cystometrograms (CMGs) were performed by slowly infusing the bladder with saline to determine the bladder capacity that was defined as the volume threshold to induce a reflex bladder contraction of large amplitude (>30 cmH$_2$O) and long duration (>20 seconds). Then, with the bladder distended at a volume about 90% of the bladder capacity (N=9 cats) PNS of 30 second duration and 1-2T intensity was repeatedly applied at different frequencies (0.5-50 Hz) in order to determine the optimal PNS frequency for inducing a large bladder contraction. At the optimal frequency (1-3 Hz), PNS of 30 second duration was applied again at different intensities (0.25-2T) to determine the intensity-response relationship (N=8 cats). After the frequency and intensity tests, multiple CMGs were performed without PNS to determine the control bladder capacity, which was followed by additional 2 CMGs performed during 1T or 2T PNS (N=8 cats). Finally, another control CMG was performed without PNS to determine any post-stimulation effect.

To determine if PNS can remove the long-lasting post-stimulation inhibition of bladder reflex activity induced by TNS, multiple control CMGs were performed again (N=5 cats). At the end of the last control CMG, TNS of 3-4T intensity was applied for 30 minutes to induce a post-stimulation inhibition that persists for at least 2 hours as shown in previous studies. After the 30-minute TNS, three CMGs were performed: (1) control CMG without stimulation; (2) CMG during PNS; (3) control CMG again to determine any post-PNS effect.

At the end of the experiment with the bladder distended at a volume about 90% of the bladder capacity (N=3 cats) electrical stimulation of 30 second duration and 2-4T intensity was repeatedly applied to the dorsal surface of the foot at different frequencies (0.5-50 Hz) in order to determine if bladder contraction can be induced by transcutaneous stimulation of the superficial peroneal nerve. The threshold intensity for foot stimulation was determined as the minimal intensity to induce either toe twitches or muscle twitches on the posterior thigh.

During the experiment, the bladder was emptied after each CMG followed by a 2-3 minute resting period to allow the bladder to recover. During the frequency and intensity tests, the 30 second PNS was applied at >60 second intervals and different frequencies/intensities were applied in a random order to minimize the potential interaction between the repeated stimulation.

Repeated measurements (2-3 CMGs) of control bladder capacity in the same animal were averaged. Then, the bladder capacity was measured during every CMG and normalized to the averaged control capacity in each cat. The amplitude, duration, and area under curve of bladder contractions were also measured in each CMG and normalized to the averaged values obtained during control CMGs in each cat. For the frequency and intensity tests, the contraction amplitude and area under the contraction curve were measured and normalized to the maximal response in each cat. The data from different animals are presented as mean±standard error. Statistical significance ($p<0.05$) was determined by repeated-measures one-way ANOVA followed by Dunnett's multiple comparison.

Results

Figure 3:
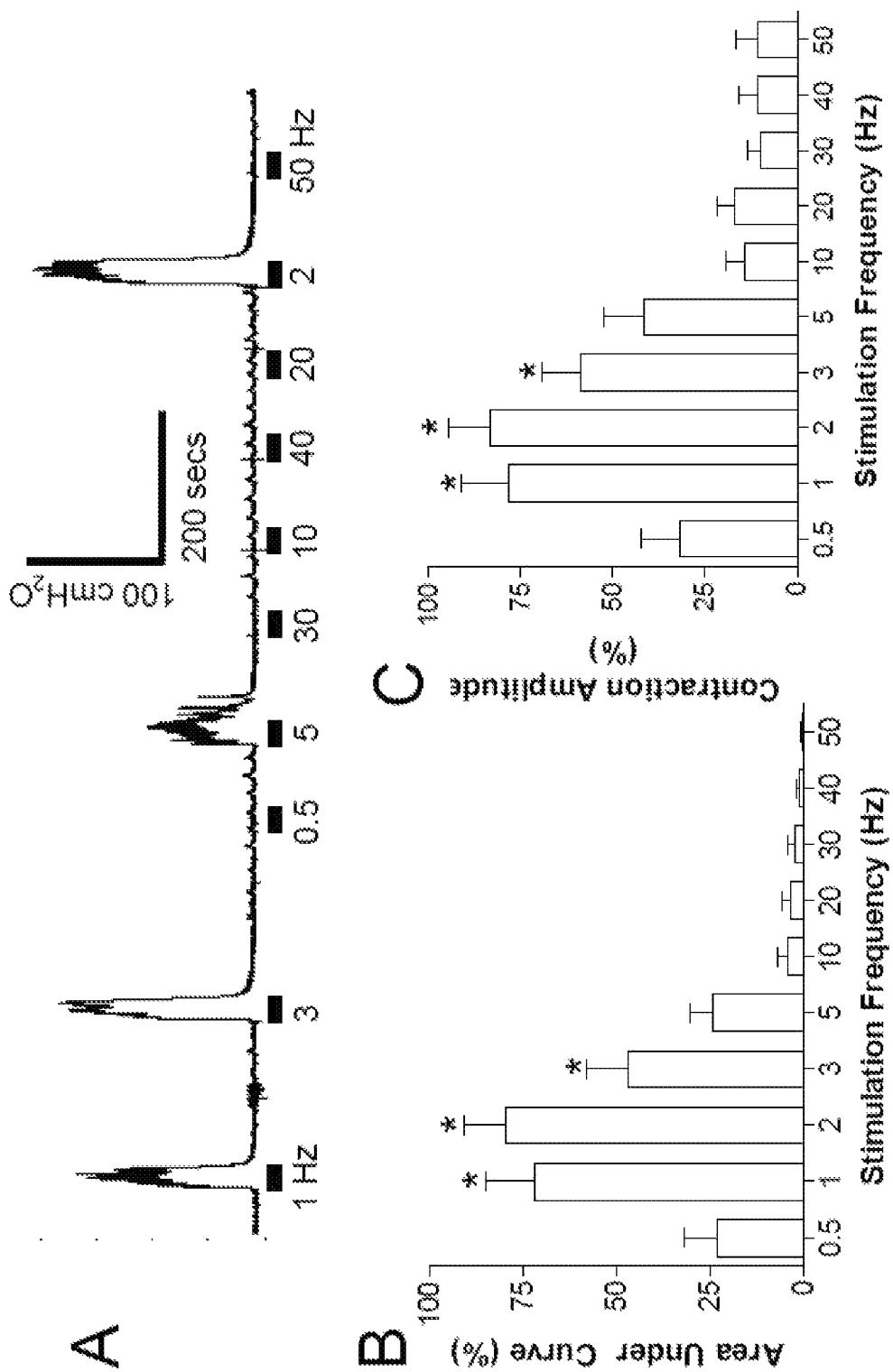
FIG. 3. Bladder pressure responses to different frequencies (0.5-50 Hz) of superficial peroneal nerve stimulation (PNS). A: Bladder pressure tracings. The black bar under the pressure tracing indicates the duration (30 secs) of PNS (0.2 ms, 1T=12 V). T—threshold intensity to induce muscle twitch on the posterior thigh. B: Normalized area under curve. C: Normalized contraction amplitude. Bladder pressure response was normalized to the maximal response in each animal (N=9 cats). * significantly (p<0.01) different from the response at 50 Hz (one-way ANOVA). PNS (0.2 ms, 1-2T, T=0.9-20 V).
Figure 4:
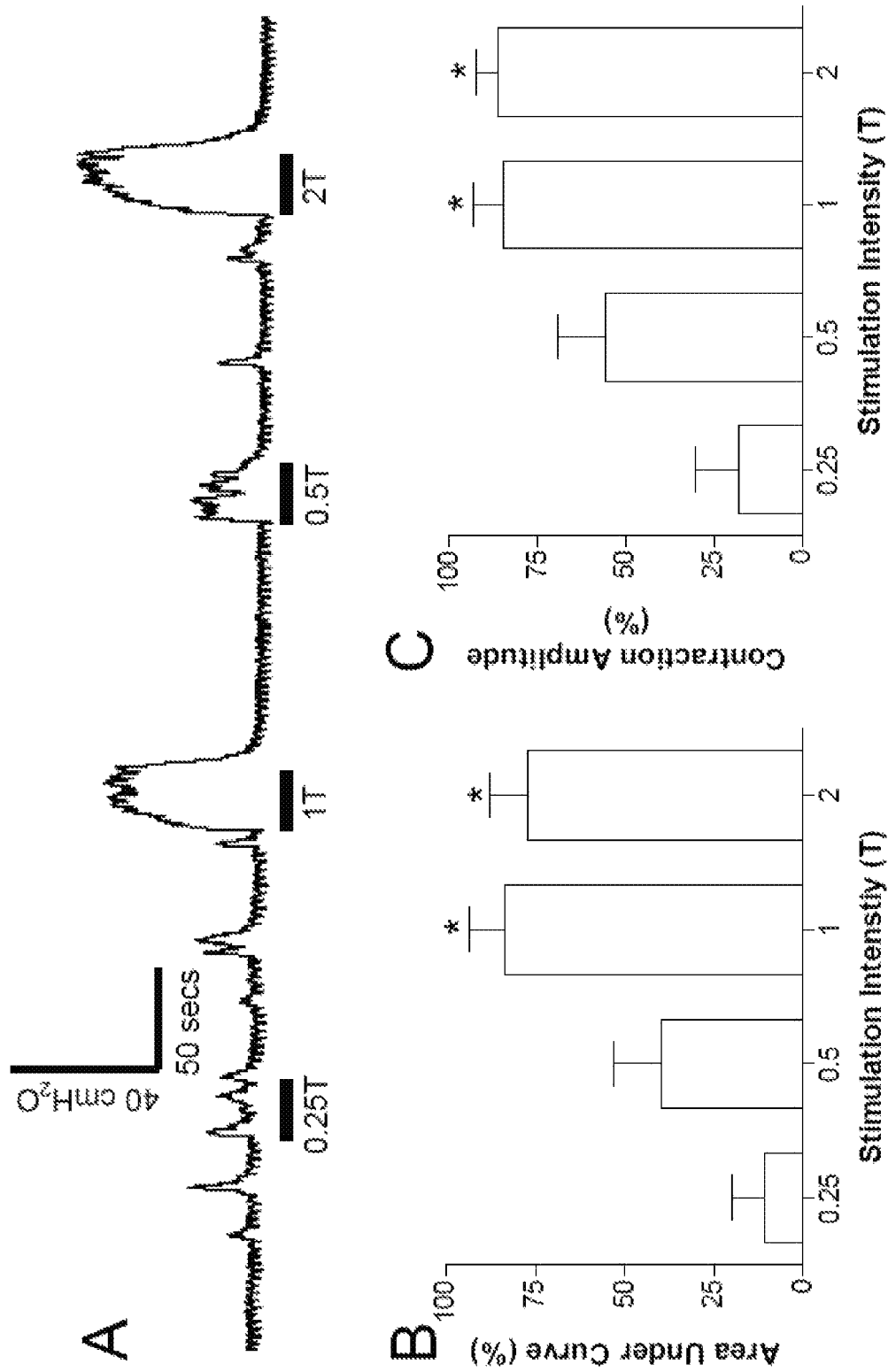
FIG. 4. Bladder pressure responses to different intensities (0.25-2T) of superficial peroneal nerve stimulation (PNS). T—threshold intensity to induce observable muscle twitch on the posterior thigh. A: bladder pressure tracings. The black bar under the pressure tracing indicates the duration (30 secs) of PNS (1 Hz, 0.2 ms, T=2.4 V). B: Normalized area under curve. C: Normalized contraction amplitude. Bladder pressure response was normalized to the maximal response in each animal (N=8 cats). * significantly (p<0.01) different from the response at 0.25T (one-way ANOVA). PNS (1-3 Hz, 0.2 ms, T=0.9-20 V).

Peroneal-to-Bladder Reflex Induced by PNS at Different Frequencies and Intensities When the bladder was distended by saline to a volume about 90% of the bladder capacity, PNS applied for 30 seconds at frequencies between 1 Hz and 3 Hz and at the threshold intensity (1T) for eliciting a muscle twitch on the posterior thigh produced large amplitude (40-150 cmH$_2$O) bladder contractions (FIG. 3, panel A and FIG. 4, panel A). As the PNS frequency was increased above 3 Hz or decreased below 1 Hz, the induced-bladder contractions were gradually reduced in amplitude and area under the curve (FIG. 3, panels B and C). At an effective frequency, PNS at 1T intensity induced a maximal bladder contraction that was not further enhanced by PNS at 2T intensity (FIG. 4).

PNS Reduced Bladder Capacity and Enhanced Reflex Bladder Contractions

Figure 5:
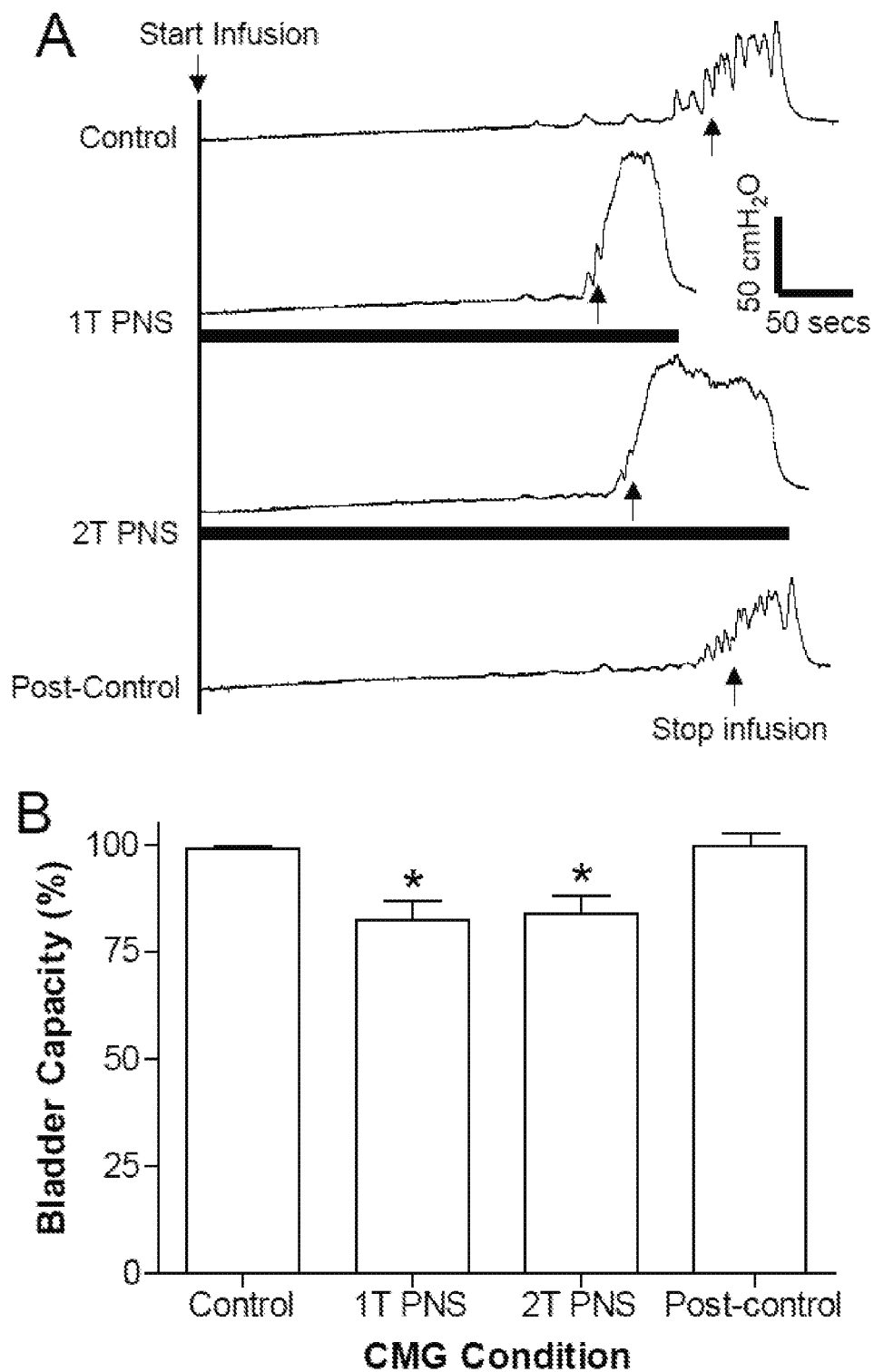
FIG. 5. Effect of superficial peroneal nerve stimulation (PNS) on bladder capacity. A: Repeated CMG tracings with/without PNS. The black bar under the bladder pressure tracing indicates the duration of PNS (1 Hz, 0.2 ms, T=8 V). T—threshold intensity to induce observable muscle twitch on the posterior thigh. Infusion rate=2 ml/min B: Summarized results (N=8 cats). Bladder capacity was normalized to the control capacity. * significantly (p<0.01) different from the control capacity (one-way ANOVA). PNS (1-3 Hz, 0.2 ms, T=1.4-20 V).
Figure 6:
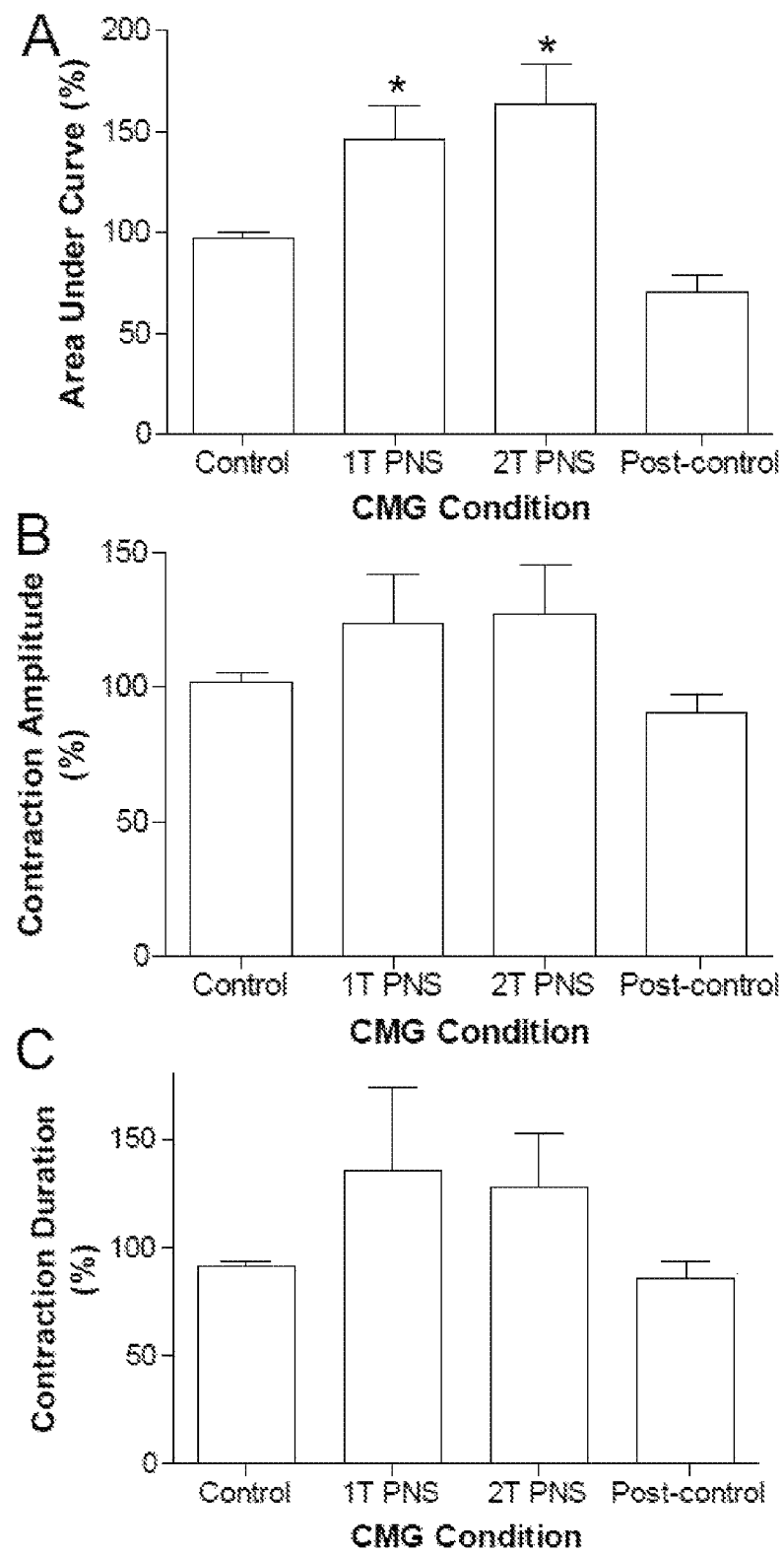
FIG. 6. Effects of superficial peroneal nerve stimulation (PNS) on bladder contraction. A: Area under the curve of bladder contraction pressure. B: Contraction amplitude. C: Contraction duration. Bladder contraction response was normalized to the control response. * significantly (p<0.05) different from control response (one-way ANOVA, N=6 cats). PNS (1-3 Hz, 0.2 ms, T=1.4-20 V). T—threshold intensity to induce observable muscle twitch on the posterior thigh.

During repeated CMGs, continuous PNS at 1-3 Hz beginning at the start of bladder filling significantly ($p<0.01$) reduced the bladder capacity to about 80% of the control capacity (FIG. 5) and significantly ($p<0.05$) increased the area under curve of the reflex bladder contractions (FIG. 6, panel A). The responses evoked by 1T or 2T PNS were not significantly different. After terminating the PNS and after a 2-3 minute recovery period the next CMG revealed that bladder capacity (FIG. 5) and contraction area under the curve (FIG. 6, panel A) returned to the original control indicating that PNS did not induce a post-stimulation effect.

PNS Removed Post-TNS Inhibition and Prolonged Reflex Bladder Contractions

Previous studies revealed that TNS for 30 minutes produces a prolonged post-stimulation inhibition of reflex bladder activity evident as an increase in bladder capacity. The inhibition can last more than 2 hours after termination of the TNS. In this study, after 30 minutes of TNS the bladder reflex activity was inhibited during the post-TNS period during which a series of three CMGs were performed over a period of 1-2 hours (FIG. 7, panel A). The bladder capacity measured during the first post-TNS CMG was significantly ($p<0.01$) increased to 140.5±7.6% of the control capacity (FIG. 7, panel B). PNS applied during the second CMG completely removed this post-TNS inhibition and restored the bladder capacity to the original control level (FIG. 7, panel A and B). PNS also significantly ($p<0.05$) increased the duration of the bladder contractions (FIGS. 7A and 8). The third CMG performed 2-3 minutes after termination of PNS indicated that the post-TNS inhibition reappeared (FIG. 7, panel A), producing a significantly larger bladder capacity than during pre-TNS control CMG (FIG. 7, panel B).

Peroneal-to-Bladder Reflex Induced by Transcutaneous Foot Stimulation

When the bladder was distended at a volume about 90% of the bladder capacity, electrical stimulation (30 seconds, 2-4T, T=3-7 V) applied to the dorsal skin surface of left foot (FIG. 9, panel B) activated the superficial peroneal nerve and induced large bladder contractions (50-100 cmH$_2$O) at frequencies of 0.5-3 Hz (FIG. 9, panel A). On average the foot stimulation at 1-2 Hz produced significantly ($p<0.05$) larger bladder contractions than the contractions elicited by other frequencies (FIG. 9, panel C and 9, panel D).

Discussion

In anesthetized cats, PNS at frequencies of 1-3 Hz and at threshold intensity (1T) for producing muscle twitch on the posterior thigh elicits bladder contractions (FIG. 3), decreases bladder capacity during CMGs (FIG. 5), and reverses the prolonged increase in bladder capacity induced by 30 minute TNS (FIG. 7). Activation of the superficial peroneal nerve by transcutaneous electrical stimulation on the dorsal surface of the foot also induces large bladder contractions (FIG. 9), raising the possibility that non-invasive electrical stimulation methods might be used clinically to trigger the excitatory peroneal-to-bladder reflex and promote voiding in patients with UAB or NOUR.

Because the superficial peroneal nerve contains a broad range of axonal subtypes, the effects of PNS on reflex bladder activity could be due to activation of cutaneous and muscle afferent axons that input directly to the spinal cord or due to activation of alpha or gamma motor axons that elicit muscle contractions that in turn activate afferent input to the spinal cord. In humans electrical stimulation of the peroneal nerve evokes reflex contractions of leg muscles in part by the latter indirect mechanism. In these cat experiments a similar indirect mechanism is likely to contribute to the large bladder reflexes elicited by PNS at 2T intensity when directly induced dorsiflexion of the foot was observed. However, at lower intensities (0.5-1T) reflex bladder contractions could be elicited without any muscle contraction or only reflex muscle contractions on the posterior thigh and therefore must have been mediated by direct activation of low threshold, large diameter group I afferent axons in the superficial peroneal nerve. These data are contrary to those obtained in a previous study in anesthetized cats where electrical stimulation of superficial and deep branches of the peroneal nerve elicited excitatory bladder reflexes only at stimulus intensities 20-100 times the threshold for group I or II afferents, leading to the conclusion that the bladder reflexes were activated by groups III and IV afferent axons, which will cause painful sensation preventing clinical application of this high intensity stimulation. These differences might be related to the type of anesthetic, i.e., chloralose in these experiments and chloralose plus urethane in the experiments of. The latter anesthetic might suppress the reflexes triggered by low intensity stimuli which were observed in these experiments.

The frequency-response curve for the excitatory peroneal-to-bladder reflex triggered by direct nerve or dorsal foot stimulation exhibited a unimodal distribution with a peak in a narrow frequency range from 1-3 Hz (FIG. 3 and FIG. 9). Sato et al. also obtained a frequency-response curve for PNS with a peak at 3-4 Hz but their curve was bimodal with a second peak at 20-30 Hz stimulation. This difference could be related to the different intensities of stimulation used in the two sets of experiments as well as the different anesthetics. Moreover, Sato utilized stimulation at extremely high intensities in order to see an effect, for example 30T and greater.

The effects on the bladder of stimulation of various hindlimb somatic nerves, including the peroneal nerve, vary with the state of the bladder. In the partially distended but quiescent bladder excitatory reflexes predominate; but when the bladder is distended under isovolumetric conditions with a volume above the micturition threshold volume and with the bladder exhibiting rhythmic contractions, inhibition predominates, which prevent voiding to occur. In contrast to Sato's results, the present results demonstrate that PNS enhanced bladder contraction when bladder volume was above the micturition threshold volume during a micturition contraction (FIG. 5, panel A and FIG. 6, panel A). The optimal frequencies for eliciting inhibition are 6-10 Hz. This range of frequencies is located between the two peaks of the excitatory bimodal frequency response curve. TNS also produces a combination of excitatory and inhibitory effects that is frequency dependent. Low frequency stimulation (2 Hz) in chloralose anesthetized cats facilitates on-going isovolumetric rhythmic bladder contractions but this study is silent in showing urethral relaxation and voiding; while higher frequencies of stimulation (5-30 Hz) as shown in FIG. 7 produces inhibition. Thus, the bladder responses to somatic afferent stimulation are complicated, varying according to the types of afferents activated (i.e., muscle or cutaneous, large or small diameter), frequency of stimulation, and the state of the bladder. This study is the first study showing that PNS can initiate bladder contraction when bladder volume is below micturition threshold volume (FIG. 3 and FIG. 9) and can enhance bladder contraction when bladder volume is above the micturition threshold volume and the micturition contraction is occurring (FIG. 5, panel A and FIG. 6, panel A). In addition, the present study shows that PNS can reduce the micturition threshold volume so that micturition contraction occurs at a smaller volume (i.e. increasing the bladder sensation) (FIG. 5). More importantly, the present study shows that PNS can restore bladder sensation to allow micturition contraction to occur at a smaller volume with a stronger contraction when the bladder is in retention requiring about 50% more bladder volume to void (FIG. 7 and FIG. 8). This is the first result showing that PNS can induce a bladder contraction when bladder is in retention and has a large volume. This is fundamentally different from inducing a bladder contraction in a normal bladder that can have a micturition reflex at a normal bladder volume. In other words, stimulation of a nerve that can induce a bladder contraction in normal bladder does not necessarily indicates that the stimulation can induce a bladder contraction when the bladder is in retention and cannot even produce a micturition contraction with a large bladder volume.

Because the bladder is innervated by sympathetic as well as parasympathetic nerves, the effects of PNS on bladder function could be mediated by a change in activity of either of these autonomic pathways. Although lumbar sympathetic nerve activity is responsive to electrical stimulation of afferent axons in various hindlimb nerves denervation experiments revealed that elimination of the sympathetic nerves did not notably change PNS-vesical reflex responses whereas transection of the parasympathetic pathway in the pelvic nerves blocked the responses. Electrophysiological studies in which reflex firing was recorded in parasympathetic efferent nerves close to the bladder revealed that single shock electrical stimulation of the peroneal nerve as well as other limb nerves including branches of the tibial nerve elicited long latency (>100 msec) reflex firing which was similar to the long latency firing mediated by the spinobulbospinal micturition reflex pathway activated by electrical stimulation of bladder afferents in the pelvic nerve revealed that trains of PNS also inhibited or enhanced activity in bladder parasympathetic nerves depending upon the state of the bladder. Thus, modulation of bladder activity by PNS must be mediated by changes in the sacral parasympathetic outflow and very likely mediated by a supraspinal reflex pathway involving the periaqueductal gray (PAG) and the pontine micturition center (PMC).

The PNS excitatory effect on the bladder could occur on both afferent and efferent limbs of the spinobulbospinal micturition reflex pathway. PNS significantly reduced bladder capacity (FIG. 5) indicating modulation of the afferent limb to either enhance bladder afferent input to the PAG-PMC or reduce the threshold in the PMC circuitry for triggering a micturition reflex (de Groat and Wickens, 2013). At the same time PNS also produces stronger bladder contractions (FIG. 5, panel A, FIG. 6, FIG. 7, panel A, and FIG. 8) indicating that it also acts on the efferent limb to amplify the PMC output to the bladder. In contrast, the TNS inhibitory effect must occur primarily on the afferent limb because previous studies in cats showed that TNS increases bladder capacity but does not reduce the amplitude of bladder contractions induced by PMC stimulation.

The opposing effects of PNS and TNS on the bladder were clearly demonstrated in this study by the ability of PNS to eliminate post-TNS inhibition (FIG. 7). However, this reversal was only transient; and the post-TNS inhibition reappeared after the PNS was terminated (FIG. 7). The mechanisms responsible for the PNS reversal of TNS inhibition are not known. The reversal could be due to a PNS activation of excitatory inputs to the bladder preganglionic neurons in the sacral spinal cord to counteract the TNS inhibition or due to a direct suppression of the inhibitory pathway activated by TNS. Whether a long-lasting post-PNS excitatory effect can be induced by a 30 minute PNS is still unknown. However, since the 30 minute TNS can induce a prolonged post-stimulation inhibition lasting more than 2 hours (FIG. 7), it is possible that a long-duration PNS might also induce a long-lasting post-stimulation excitatory effect on bladder reflex.

The superficial peroneal nerve and tibial nerve innervate the dorsal and plantar surfaces of the foot and elicit opposite motor responses producing dorsiflexion and plantarflexion of the foot, respectively. Therefore, it is possible that the dorsiflexion/plantarflexion induced by PNS/TNS or the afferent firing that induces these flexor and extensor reflexes have opposite effects on the bladder. The possibility that extensor and flexor reflex mechanisms might exert reciprocal modulatory effects on the lower urinary tract was raised by a previous study in rats and cats showing that the external urethral sphincter (EUS) can be excited by triggering a flexor hindlimb reflex but inhibited by triggering an extensor reflex. The effects on EUS by PNS/TNS are currently unknown; however because the EUS and bladder exhibit reciprocal activities during urinary storage and voiding, it would be interesting in future experiments to determine if TNS which induces plantarflexion and bladder inhibition excites the EUS; while PNS which produces dorsiflexion and bladder excitation inhibits the EUS. It will also be important to determine if PNS can facilitate voiding and increase voiding efficiency by targeting the bladder and EUS. This could not be tested in the present study because voiding was blocked by ligating the urethral outlet in order to measure bladder activity under isovolumetric conditions.

The somato-visceral interactions that underlie the antagonistic effects of PNS/TNS on reflex bladder function create an animal model that mimics some of the features of Fowler's syndrome, an unusual clinical disorder characterized by NOUR. Patients with this disorder have a hyperactive EUS that triggers abnormal somatic afferent nerve activity which is conveyed through the pudendal nerve to the sacral spinal cord. It is believed that the pudendal afferent activity suppresses the bladder sensory and motor pathways thereby reducing the patient's ability to sense bladder filling and to voluntarily void. Electrical stimulation of somatic afferent axons in a sacral spinal nerve (a procedure termed sacral neuromodulation) suppresses the inhibition induced by pudendal afferents and restores bladder sensations and voiding. This pathophysiology and treatment is similar, respectively, to the TNS inhibition and the reversal of that inhibition by PNS in the cat model. Thus, post-TNS inhibition might be a useful animal model for certain types of UAB/NOUR conditions. Furthermore, the efficacy of PNS in reversing post-TNS inhibition raises the possibility that PNS might be useful clinically in treating some types of UAB/NOUR.

In summary, this study in anesthetized cats discovered an excitatory peroneal-to-bladder reflex that can reverse a long lasting somato-bladder inhibitory mechanism. This new reflex raises many scientific questions about the interactions of visceral and somatic reflex pathways and also provides potential opportunities to develop novel neuromodulation therapies for UAB/NOUR. The superficial peroneal nerve which can be activated non-invasively by skin surface electrodes on the foot, makes the peroneal-to-bladder reflex pathway an attractive target for potential clinical applications.

Example 2—Saphenous Nerve Stimulation

Methods

The experimental protocol and animal use in this study were approved by the Animal Care and Use Committee at the University of Pittsburgh.

A total of 6 cats (3 males and 3 females, 3-4.3 kg; Liberty Research, Waverly, N.Y.) were used in this study. The animals were anesthetized with isoflurane (2-5% in oxygen) during surgery and then switched to α-chloralose anesthesia (initial 65 mg/kg i.v. and supplemented as needed) during data collection. The left cephalic vein was catheterized for administration of anesthetics and fluid. A tracheotomy was performed and a tube was inserted to keep the airway patent. A catheter was inserted into the right carotid artery to monitor systemic blood pressure. Heart rate and blood oxygen were monitored by a pulse oximeter (9847V; NONIN Medical, Plymouth, Minn.) attached to the tongue. Through an abdominal incision, the ureters were isolated, tied, and cut for external drainage. A double lumen catheter was inserted into the bladder via a small cut on the proximal urethra and secured by a ligature around the urethra. One lumen was connected to a pump to slowly (1-3 ml/min) infuse saline for bladder distention. The other lumen was attached to a pressure transducer to measure bladder pressure. The saphenous nerve on the right side was exposed via a skin incision on the medial thigh slightly above the knee. The tibial nerve on the left side was dissected via skin incision at the ankle. Tripolar cuff electrodes (NC223pt, MicroProbe, Gaithersburg, Md.) were implanted on these nerves and then the electrodes were connected to a dual channel electrical stimulator (S88; Grass Medical Instruments, Quincy, Mass.) via constant voltage stimulus isolators (SIU5; Grass Medical Instruments). After the surgery, the skin and muscle layers were closed by sutures.

At the beginning of each experiment, uniphasic rectangular pulses (1 Hz frequency) were used to determine the intensity threshold (T) for saphenous nerve stimulation (SNS) to induce observable muscle twitches on the posterior thigh, hip, or toe. It is presumed that T represents the threshold for activating the largest diameter (Aβ) afferent axons in the nerve because these afferents elicit flexor reflexes in chloralose anesthetized cats. At the threshold intensity determined by 1 Hz SNS, the muscle twitches disappeared when SNS frequency was increased above 2 Hz. Based on previous studies, the intensity threshold (T) for tibial nerve stimulation (TNS) to induce observable toe twitches was determined at 5 Hz frequency. Pulse width of 0.2 ms was used for both SNS and TNS.

Initially, multiple cystometrograms (CMGs) were performed by slowly infusing the bladder with saline to determine the bladder capacity that was defined as the volume threshold to induce a micturition reflex contraction of large amplitude (>30 cmH$_2$O) and long duration (>20 seconds). Once the control bladder capacity was determined, additional 2 CMGs were performed during SNS (1 Hz, 0.2 ms, 2-4T intensity, N=6 cats). For the first CMG, SNS was applied intermittently (60 second off and 30 second on) starting at the beginning of the CMG and ending with the onset of the micturition reflex at which time the stimulation was switched to continuous stimulation that continued for the duration of the micturition contraction. This stimulation pattern (intermittent continuous) is termed as SNSi-c in this study (see FIG. 11). For the second CMG, continuous SNS (SNSc) was applied at the beginning and maintained until the end of the CMG. The purpose of testing SNSi-c was to determine if prolonged SNSc during the storage phase produces fatigue and therefore has less effect on bladder capacity than SNSi-c which might be expected to produce less fatigue. SNS was terminated in some experiments before the reflex contraction ended to prevent bladder over distension when the contraction duration reached 3 times the control contraction duration. Following the two CMGs with SNS, another control CMG was performed without SNS to determine any post-stimulation effect.

Then, the experiments were continued to determine if SNS could facilitate the micturition reflex during the long-lasting post-stimulation inhibition induced by TNS. Multiple control CMGs were performed again. At the end of the last control CMG, TNS (5 Hz, 0.2 ms, 4-8T intensity, 30-minute duration) was applied 1-8 times in different animals to significantly increase bladder capacity and reduce (>40%) the amplitude of the micturition contraction. The prolonged post-TNS inhibition induced by 30-minute TNS can last for at least 2 hours as shown in previous studies. After the repeated 30-minute TNS, four CMGs were performed: (1) control CMG without stimulation; (2) CMG with SNSi-c (60-second off and 30-second on during storage phase but continuous during the micturition contraction); (3) CMG with SNSc (continuous SNS during both the storage phase and micturition contraction); (4) control CMG again to determine any post-stimulation effect. During the repeated CMG testing, the bladder was emptied after each CMG followed by a 2-3 minute resting period to allow the bladder to recover.

At the end of the experiment with the bladder fully distended at the bladder capacity and contracting rhythmically (N=5 cats), SNS (10 V, 0.2 ms, 30-second duration) at different frequencies (0.5-30 Hz) was repeatedly applied to determine the frequency response. Then, SNS (1 Hz, 0.2 ms, 30-second duration) at different intensities (0.25-10 V) was repeatedly applied to determine the intensity response. During the frequency and intensity tests, a rest period (>60 seconds) followed each 30-second SNS.

Results

Facilitation of the Normal Micturition Reflex by 1-Hz SNS

SNS applied continuously (SNSc) or intermittently (SNSi-c) starting at the beginning of the CMG and continuing until the initiation of the normal micturition reflex did not change bladder capacity (FIG. 11 and FIG. 12). However, when the SNSc was continued or when the SNSi-c became continuous immediately after the initiation of the micturition reflex, the duration of bladder contraction significantly increased to 236.9±45.7% ($p<0.01$) or 211.4±46.3% ($p<0.05$) of control duration, respectively (FIG. 11 and FIG. 12). SNSi-c (3 cats) and SNSc (1 cat) were terminated early to avoid bladder over-distension when the contraction duration reached 3 times the control duration (see second trace in FIG. 11). These effects of SNSi-c and SNSc on bladder contraction duration were not significantly different (FIG. 12). On average the duration of the bladder contractions recovered to the pre-SNS level indicating that there was no statistically significant post-SNS effect (FIG. 12). The amplitude of the bladder contraction was not significantly changed by either SNSi-c or SNSc (FIG. 11 and FIG. 12).

SNS at 1 Hz Normalized Bladder Underactivity During Post-TNS Inhibition

Repeated (1-8 times) application of 30-minute TNS at intensities 4-8 times the threshold to induce observable toe twitches significantly increased bladder capacity and reduced (>40%) the amplitude of the micturition reflex contraction in 5 of the 6 cats. In 3 of these animals, a micturition reflex contraction did not occur even when the baseline bladder pressure reached 40 cmH$_2$O during the CMG, indicating complete urinary retention. On average, repeated application of 30-minute TNS significantly ($p<0.01$) increased bladder capacity to 135.9±7.6% (FIG. 14) and decreased amplitude of the micturition contraction to 44.1±16.5% (FIG. 14) of pre-TNS control, producing a type of bladder underactivity characterized by a large bladder capacity with a reduced bladder contraction amplitude. However, the post-TNS inhibition did not significantly ($p>0.05$) change the duration of the bladder contractions (FIG. 14). During the post-TNS inhibition, SNSi-c and SNSc applied during CMGs normalized the bladder underactivity by significantly reducing the bladder capacity (FIG. 13 and FIG. 14) to 100.2±7.0% ($p<0.01$) and 113.9±7.2% ($p<0.05$) of control and increasing the amplitude of the contractions (FIG. 13 and FIG. 14) to 111.3±17.0% ($p<0.01$) and 91.0±12.5% ($p<0.05$) of control, respectively. In addition, SNSi-c and SNSc also increased the duration of the contractions (FIG. 14) to 201.5±61.3% ($p<0.01$) and 185.5±55.6% ($p<0.05$) of control, respectively. These effects of SNSi-c and SNSc were not significantly different. Within 20 minutes after termination of the stimulation the bladder capacity as well as the amplitude and duration of the bladder contractions returned to the pre-SNS levels indicating that there was no post-SNS effect (FIG. 13 and FIG. 14).

Effects of SNS Frequency and Intensity on Micturition Reflex

At the end of the experiment with the bladder fully distended and contracting rhythmically, 30-second duration trains of SNS (10V, 0.2 ms) at frequencies of 0.5-2 Hz induced significantly ($p<0.05$) larger bladder contractions (FIG. 15) than those induced by 30-Hz stimulation.

SNS at 1 Hz induced significantly ($p<0.05$) larger bladder contractions at intensities of 2-10 V than 0.25 V (FIG. 15). The range of stimulus intensities for evoking reflex contractions of hind limb muscles in these experiments (i.e., the motor threshold intensity, T) was 2.5-5 V (N=5 cats). In one cat, muscle twitches were not elicited at SNS intensities ranging up to 80 V and therefore the motor threshold T could not be determined. In this cat, 10 V was used to test SNS effects, which was the upper limit of the 2-4T (7-10 V) used in other cats. This comparison of stimulus intensity thresholds (FIG. 15) showed that on average a significantly larger bladder contraction could be induced by 1-Hz SNS at an intensity (2 V) slightly below the motor threshold T (2.5-5 V).

Example 3—Tibial Nerve Stimulation

Methods

The experimental protocol and animal use in this study were approved by the Animal Care and Use Committee at the University of Pittsburgh.

A total of 10 cats (5 male and 5 female, 2.6-4.2 kg; Liberty Research, Waverly, N.Y.) were used in this study. The animals were anesthetized with isoflurane (2-5% in oxygen) during surgery and then switched to α-chloralose anesthesia (initial 65 mg/kg intravenous and supplemented as needed) during data collection. Left cephalic vein was catheterized for administration of anesthetics and fluid. A tracheotomy was performed and a tube was inserted to keep the airway patent. A catheter was inserted into right carotid artery to monitor systemic blood pressure. Heart rate and blood oxygen were monitored by a pulse oximeter (9847V; NONIN Medical, Plymouth, Minn.) attached to the tongue. Through an abdominal incision, the ureters were isolated, tied, and cut for external drainage. A double lumen catheter was inserted into the bladder via a small cut in the proximal urethra and secured by a ligature around the urethra. One lumen of the catheter was connected to a pump to slowly infuse (1-2 ml/min) the bladder with saline or 0.25% acetic acid (AA). The other lumen was connected to a pressure transducer to measure the pressure change in the bladder. The tibial nerves were exposed at the left and right ankles. Tripolar cuff electrodes (NC223pt, MicroProbe, Gaithersburg, Md.) were implanted on each tibial nerve for stimulation. Each cuff electrode was connected to an electrical stimulator (S88; Grass Medical Instruments, Quincy, Mass.) via a constant voltage stimulus isolator (SIU5; Grass Medical Instruments). The temperature of the animal was maintained at 36-38° C. using a heating pad during the experiments. The surgical incisions including the skin and muscle layers were closed with sutures.

Uniphasic rectangular pulses (0.2 ms pulse width) were delivered via the cuff electrodes. At the beginning of the experiment, the intensity threshold (T) for inducing observable toe movement was determined by gradually increasing stimulation intensity at 1 Hz on the right tibial nerve and 5 Hz on the left tibial nerve. Multiples of the threshold intensity were then used during the experiment. The left tibial nerve was only stimulated at 5 Hz. The right tibial nerve was always stimulated at 1 Hz except when different stimulation frequencies (0.5-30 Hz) were applied to examine frequency response relationships. At the beginning of the study, repeated cystometrograms (CMGs) were performed by slowly infusing the bladder with saline to determine bladder capacity which was defined as the volume required to induce a reflex bladder contraction of large amplitude (>30 cmH$_2$O) and long duration (>20 seconds). Once bladder capacity stabilized, an additional 2 CMGs were performed during TNS (1 Hz, 0.2 ms, 4T intensity) applied on the right side (N=9 cats). For the first CMG, TNS was applied intermittently (60 second off and 30 second on) starting at the beginning of the CMG and ending with the onset of the micturition reflex at which time the stimulation was switched to continuous stimulation that continued for the duration of the micturition contraction. This stimulation pattern (intermittent-continuous) is termed TNSi-c in this study (see FIG. 16). For the second CMG, continuous TNS (TNSc) was applied at the beginning and maintained until the end of the CMG. The purpose of testing TNSi-c was to determine if prolonged TNSc during the storage phase produces fatigue and therefore has less effect on bladder capacity than TNSi-c which might be expected to produce less fatigue. Following the two CMGs with TNS, another control CMG was performed without TNS to determine any post-stimulation effect. During the repeated CMG tests, a 2-3 minute resting period was always inserted between the CMGs.

After testing the TNS in normal bladders, the effect of 1 Hz TNS on bladder underactivity was further examined (N=8 cats). The animal's bladders were made areflexic or poorly reflexic by repeated application (2-6 times) of 30-minute TNS (5 Hz, 4-8T, 0.2 ms) to the left tibial nerve until the post-TNS CMG showed either no bladder reflex during filling up to intravesical pressures of 30-40 cmH$_2$O, or a bladder reflex that occurred at >150% of control capacity. Previous studies in cats revealed that the post-TNS inhibition of reflex bladder activity persists for at least two hours. Once this type of bladder underactivity was achieved, 3 CMGs were performed: (1) CMG during 1 Hz TNSi-c applied on the right side; (2) CMG during 1 Hz TNSc applied on the right side; and (3) Control CMG to examine any post-stimulation effect. TNS (1 Hz) was terminated in some experiments before the reflex contraction ended to prevent bladder over distension when the contraction duration reached more than 2.5 times the control contraction duration.

After testing 1 Hz TNS during CMGs, the frequency and intensity effect of TNS on bladder underactivity were further tested under isovolumetric conditions with the bladder fully distended (N=4 cats). TNS of short duration (30 seconds) was applied to the right tibial nerve at different frequencies (0.5-30 Hz at 4T) or different intensities (0.25-4T at 1 Hz) with an interval of >60 seconds between any two applications.

At the end of the study, the effect of 1 Hz and 5 Hz TNS on bladder overactivity was examined (N=6 cats). Repeated CMGs were performed by infusing 0.25% AA to irritate the bladder and induce bladder overactivity, which markedly reduced the bladder capacity. Once the irritated small bladder capacity stabilized, 3 CMGs were performed during AA infusion: (1) CMG during continuous 1 Hz TNS (4T intensity) applied to the right tibial nerve; (2) CMG during continuous 5 Hz TNS (4T intensity) applied to the left tibial nerve; and (3) Control CMG to examine any post-stimulation effect.

Results

Effect of 1 Hz TNS on Normal Bladder Reflex Activity

1 Hz TNS (4T, 0.2 ms) had no effect on bladder capacity when it was applied intermittently (TNSi-c) during saline infusion (FIG. 16), while on average the bladder capacity was slightly increased when 1 Hz TNS was applied continuously (TNSc) (FIG. 16). Neither TNSi-c nor TNSc altered the amplitude of the micturition contraction (FIG. 16 and FIG. 17). However, the duration of the micturition contraction was significantly ($p<0.01$) increased to 180.7±18.5% and 160.4±25.5% of control duration by TNSi-c and TNSc, respectively (FIG. 16 and FIG. 17). The effects produced by TNSi-c and TNSc on contraction duration were not significantly different (FIG. 16 and FIG. 17).

Effect of 1 Hz TNS on the Underactive Bladder Reflex Activity Induced by Prolonged 5 Hz TNS Repeated application (2-6 times) of 30-minute TNS (5 Hz, 4-8T, 0.2 ms) induced poststimulation inhibition which blocked the large amplitude micturition reflex in 4 of 8 cats tested even when the bladder pressure reached 30-40 cmH$_2$O during a CMG (see the second CMG in FIG. 18A). In the other 4 cats, the micturition reflex still occurred but the bladder capacity was increased to >150% of control capacity. On average the prolonged 5 Hz TNS significantly ($p<0.01$) increased the bladder capacity to 173.8±10.4% of control (FIG. 18B) and reduced the contraction amplitude to 40.1±15.3% of control (FIG. 19), but did not significantly change contraction duration (FIG. 19

TNSi-c and TNSc (1 Hz, 4T, 0.2 ms) reversed the 5 Hz TNS-induced bladder underactivity by significantly ($p<0.01$) reducing the capacity to 130.9±5.8% and 143.1±9.5% of control (FIG. 18B) and restoring the contraction amplitude to 104.7±6.4% and 96.7±5.6% of control (FIG. 19), respectively. The 1 Hz TNSi-c also significantly ($p<0.05$) increased the contraction duration to 171.7±27% of control (FIG. 19). In 2 cats, the 1 Hz TNSi-c was terminated early before the contraction ended since the duration of contraction reached >250% of control (see the third CMG in FIG. 18A. In one cat, the 1 Hz TNSc was also terminated before the contraction ended due to a long duration of contraction. Within 10-15 minutes after the 1 Hz TNSi-c or TNSc the bladder underactivity returned (see the fifth CMG trace in FIG. 18A and control 3 bars in FIG. 18B and FIG. 19), indicating that the post-TNS inhibition induced by 5 Hz stimulation was longlasting. In 2 of the 4 cats with areflexic bladders, a weak bladder reflex reappeared with a contraction amplitude less than 50% of control and a large bladder capacity during the poststimulation period after the 1 Hz TNSi-c and TNSc (see the control 3 CMG in FIGS. 20-22).

Frequency and Intensity Effects of TNS on Bladder Underactivity

The effects of various frequencies and intensities of TNS on bladder underactivity were tested under isovolumetric conditions when the bladder was fully distended and exhibited small or no reflex contractions (FIGS. 20-22). TNS (4T, 0.2 ms) of 30-second duration and in a range of frequencies (0.5-3 Hz) induced significantly ($p<0.05$) larger contractions (FIGS. 20-22), while TNS at 1 Hz induced significantly ($p<0.05$) larger contractions when the intensity was at or greater than 1T (FIGS. 20-22).

Effects of 1 Hz and 5 Hz TNS on Overactive Bladder Reflex Activity

Infusion of 0.25% AA irritated the bladder and elicited bladder overactivity indicated by a significantly ($p<0.01$) reduced bladder capacity that was only 42.8±4.2% of the control capacity measured during saline infusion before application of any TNS (FIG. 23 and FIG. 24). Subsequent 1 Hz TNS (4T) did not significantly change the bladder capacity. However, 5 Hz TNS significantly ($p<0.01$) increased bladder capacity to 85.2±8.2% of saline control (FIG. 23 and FIG. 24). There was no post-TNS effect on bladder capacity. In addition, the amplitude and duration of bladder contractions were not significantly changed by either AA irritation or TNS when compared to the measurements during saline control conditions. The effect of 1 Hz TNS to smooth the contraction and increase the area under the contraction curve (see FIG. 23) was only observed in 2 of the 6 cats tested.

Example 4—Sural Nerve Stimulation

A set of experiments was conducted as described above, with stimulation delivered to the sural nerve instead of superficial peroneal nerve (FIG. 1). Tibial nerve stimulation was carried out for 30 minutes at a 6T (3V, 0.5 Hz frequency, 0.2 ms pulsewidth) (FIG. 25, arrows). Sural nerve stimulation was carried out at 1 Hz, 0.2 ms pulsewidth, 80 V (FIG. 25, black bars under traces). Results are presented in FIGS. 25-32 showing that: 1. Sural nerve stimulation at a frequency less than 5 Hz (0.5-2 Hz) and an intensity (2-10 V) that is at or below motor threshold can induce or enhance bladder contractions (FIG. 25); 2. When the bladder is in retention that is produced by post-TNS (5 Hz) inhibition, sural nerve stimulation (1-2 Hz) can remove the inhibition, treat retention, and produce a strong micturition contraction at a smaller bladder volume (FIGS. 26-32). These results indicate clinical applications of sural nerve stimulation to treat UAB or urinary retention.

The following clauses are illustrative of various aspects of the invention:

Clause 1: A method of increasing bladder sensation or eliciting voiding to treat underactive bladder or urinary retention in a patient in need thereof comprising stimulating a peripheral nerve of a patient with electrical stimulation comprising pulses having a pulsewidth of 0.01 ms to 3 ms, an intensity of greater than 0T and less than 5T, where T is a threshold intensity to induce a muscle twitch, and delivered at a frequency of 0.5 Hz to 3 Hz Clause 2: The method of clause 1, wherein the stimulation comprises electrical pulses having a pulsewidth of 0.2 ms, an intensity of 1T to 2T, and delivered at a frequency of 1 Hz to 2 Hz.

Clause 3: The method of clause 1 or clause 2, wherein the stimulation comprises electrical pulses having a pulsewidth of 0.2 ms, an intensity of 1T, and delivered at a frequency of 1 Hz.

Clause 4: The method of clause 1 or clause 2, wherein the stimulation comprises electrical pulses having a pulsewidth of 0.2 ms, an intensity of 1T, and delivered at a frequency of 2 Hz.

Clause 5: The method of clause 1 or clause 2, wherein the stimulation comprises electrical pulses having a pulsewidth of 0.2 ms, an intensity of 2T, and delivered at a frequency of 1 Hz.

Clause 6: The method of clause 1 or clause 2, wherein the stimulation comprises electrical pulses having a pulsewidth of 0.2 ms, an intensity of 2T, and delivered at a frequency of 2 Hz.

Clause 7: The method of any of clauses 1-6, wherein the stimulation is applied through one or more electrodes on the skin on the dorsal surface of the patient's foot.

Clause 8: The method of clause 7, wherein the one or more electrodes comprise a cathodal electrode and an anodal electrode.

Clause 9: The method of clause 7 or clause 8, wherein at least one of the electrodes overlays the superficial peroneal nerve or its branches.

Clause 10: The method of clause 7 or clause 8, wherein at least one of the electrodes overlays the deep peroneal nerve or its branches.

Clause 11: The method of clause 7 or clause 8, wherein at least one of the electrodes overlays the saphenous nerve or its branches.

Clause 12: The method of clause 7 or clause 8, wherein at least one of the electrodes overlays the sural nerve or its branches.

Clause 13: The method of any of clauses 1-6, wherein the stimulation is applied through one or more electrodes on the skin on the patient's ankle.

Clause 14: The method of clause 13, wherein the one or more electrodes comprise a cathodal electrode and an anodal electrode.

Clause 15: The method of clause 13 or clause 14, wherein at least one of the electrodes overlays the sural nerve or its branches.

Clause 16: The method of clause 13 or clause 14, wherein at least one of the electrodes overlays the tibial nerve or its branches.

Clause 17: The method of any of clauses 1-6, wherein the stimulation is applied through one or more electrodes on the skin on the plantar surface of the patient's foot.

Clause 18: The method of clause 17, wherein the one or more electrodes comprise a cathodal electrode and an anodal electrode.

Clause 19: The method of clause 17 or clause 18, wherein at least one of the electrodes overlays the medial plantar nerve, lateral plantar nerve, or their branches.

Clause 20: The method of any of clauses 1-6, wherein the stimulation is applied through one or more electrodes on the skin on the patient's leg.

Clause 21: The method of clause 20, wherein the one or more electrodes comprise a cathodal electrode and an anodal electrode.

Clause 22: The method of clause 20 or clause 21, wherein at least one of the electrodes overlays the tibial nerve or its branches.

Clause 23: The method of clause 20 or clause 21, wherein at least one of the electrodes overlays the femoral cutaneous nerve or its branches.

Clause 24: The method of clause 20 or clause 21, wherein at least one of the electrodes overlays the saphenous nerve or its branches.

Clause 25: The method of clause 20 or clause 21, wherein at least one of the electrodes overlays the superficial peroneal nerve or its branches.

Clause 26: The method of clause 20 or clause 21, wherein at least one of the electrodes overlays the deep peroneal nerve or its branches.

Clause 27: The method of clause 20 or clause 21, wherein at least one of the electrodes overlays the sural nerve or its branches.

Clause 28: The method of any of clauses 1-6, wherein the stimulation is applied through one or more surgically implanted electrodes configured on or near one or more of the superficial peroneal nerve, the deep peroneal nerve, the saphenous nerve, the sural nerve, the tibial nerve, and/or the femoral cutaneous nerve.

Clause 29: A method of increasing bowel sensation or eliciting defecation to treat infrequent bowel movements or constipation in a patient in need thereof comprising stimulating a peripheral nerve of a patient with electrical stimulation comprising pulses having a pulsewidth of 0.01 ms to 3 ms, an intensity of greater than 0T and less than 5T, where T is a threshold intensity to induce a muscle twitch, and delivered at a frequency of 0.5 Hz to 3 Hz.

Clause 30: The method of clause 29, wherein the stimulation comprises electrical pulses having a pulsewidth of 0.2 ms, an intensity of 1T to 2T, and delivered at a frequency of 1 Hz to 2 Hz.

Clause 31: The method of clause 29, wherein the stimulation comprises electrical pulses having a pulsewidth of 0.2 ms, an intensity of 1T, and delivered at a frequency of 1 Hz.

Clause 32: The method of clause 29, wherein the stimulation comprises electrical pulses having a pulsewidth of 0.2 ms, an intensity of 1T, and delivered at a frequency of 2 Hz.

Clause 33: The method of clause 29, wherein the stimulation comprises electrical pulses having a pulsewidth of 0.2 ms, an intensity of 2T, and delivered at a frequency of 1 Hz.

Clause 34: The method of clause 29, wherein the stimulation comprises electrical pulses having a pulsewidth of 0.2 ms, an intensity of 2T, and delivered at a frequency of 2 Hz.

Clause 35: The method of one of clauses 29-34, wherein the stimulation is applied through one or more electrodes on the skin on the dorsal surface of the patient's foot.

Clause 36: The method of clause 35, wherein the one or more electrodes comprise a cathodal electrode and an anodal electrode.

Clause 37: The method of clause 35 or clause 36, wherein at least one of the electrodes overlays at least one of the superficial peroneal nerve, the deep peroneal nerve, the saphenous nerve, the sural nerve, and/or their branches.

Clause 38: The method of any of clauses 29-34, wherein the stimulation is applied through one or more electrodes on the skin on the plantar surface of the patient's foot.

Clause 39: The method of clause 38, wherein the one or more electrodes comprise a cathodal electrode and an anodal electrode.

Clause 40: The method of clause 38 or clause 39, wherein at least one of the electrodes overlays at least one of the medial plantar nerve, lateral plantar nerve, and/or their branches.

Clause 41: The method of any of clauses 29-34, wherein the stimulation is applied through one or more electrodes on the skin of the patient's leg.

Clause 42: The method of clause 41, wherein the one or more electrodes comprise a cathodal electrode and an anodal electrode.

Clause 43: The method of clause 41 or clause 42, wherein at least one of the electrodes overlays at least one of the superficial peroneal nerve, the deep peroneal nerve, the saphenous nerve, the sural nerve, the tibial nerve, and/or the femoral cutaneous nerve.

Clause 44: The method of any of clauses 29-34, wherein the stimulation is applied through one or more surgically implanted electrodes configured on or near one or more of the superficial peroneal nerve, the deep peroneal nerve, the saphenous nerve, the sural nerve, the tibial nerve, and/or the femoral cutaneous nerve.

Clause 45: A device for delivering electrical stimulation to a foot or leg of a patient for treating underactive bladder, urinary retention, infrequent bowel movement, or constipation in a patient in need thereof, comprising: a pulse generator; and one or more electrodes in communication with the pulse generator, wherein the pulse generator is a fixed output pulse generator configured to deliver electrical pulses having a pulsewidth of 0.01 ms to 3 ms, an intensity of greater than 0T and less than 5T, where T is a threshold intensity to induce a muscle twitch, and delivered at a frequency of 0.5 Hz to 3 Hz.

Clause 46: The device of clause 45, wherein the pulse generator is configured to deliver electrical pulses having a pulsewidth of 0.2 ms, an intensity of 1T to 2T, and delivered at a frequency of 1 Hz to 2 Hz.

Clause 47: The device of clause 45, wherein the pulse generator is configured to deliver electrical pulses having a pulsewidth of 0.2 ms, an intensity of 1T, and delivered at a frequency of 1 Hz.

Clause 48: The device of clause 45, wherein the pulse generator is configured to deliver electrical pulses having a pulsewidth of 0.2 ms, an intensity of 1T, and delivered at a frequency of 2 Hz.

Clause 49: The device of clause 45, wherein the pulse generator is configured to deliver electrical pulses having a pulsewidth of 0.2 ms, an intensity of 2T, and delivered at a frequency of 1 Hz.

Clause 50: The device of clause 45, wherein the pulse generator is configured to deliver electrical pulses having a pulsewidth of 0.2 ms, an intensity of 2T, and delivered at a frequency of 2 Hz.

Clause 51: A method of eliciting voiding to treat detrusor-sphincter dyssynergia in a patient with spinal cord injury thereof comprising stimulating a peripheral nerve of a patient with electrical stimulation comprising pulses having a pulsewidth of 0.01 ms to 3 ms, an intensity of greater than 0T and less than 5T, where T is a threshold intensity to induce a muscle twitch, and delivered at a frequency of 0.5 Hz to 3 Hz.

Clause 52: The method of clause 51, wherein the stimulation comprises electrical pulses having a pulsewidth of 0.2 ms, an intensity of 1T to 2T, and delivered at a frequency of 1 Hz to 2 Hz.

Clause 53: The method of clause 51, wherein the stimulation comprises electrical pulses having a pulsewidth of 0.2 ms, an intensity of 1T, and delivered at a frequency of 1 Hz.

Clause 54: The method of clause 51, wherein the stimulation comprises electrical pulses having a pulsewidth of 0.2 ms, an intensity of 1T, and delivered at a frequency of 2 Hz.

Clause 55: The method of clause 51, wherein the stimulation comprises electrical pulses having a pulsewidth of 0.2 ms, an intensity of 2T, and delivered at a frequency of 1 Hz.

Clause 56: The method of clause 51, wherein the stimulation comprises electrical pulses having a pulsewidth of 0.2 ms, an intensity of 2T, and delivered at a frequency of 2 Hz.

Clause 57: The method of any of clauses 51-56, wherein the stimulation is applied through one or more electrodes on the skin on the dorsal surface of the patient's foot.

Clause 58: The method of clause 57, wherein the one or more electrodes comprise a cathodal electrode and an anodal electrode.

Clause 59: The method of clause 57 or clause 58, wherein at least one of the electrodes overlays the superficial peroneal nerve or its branches.

Clause 60: The method of clause 57 or clause 58, wherein at least one of the electrodes overlays the deep peroneal nerve or its branches.

Clause 61: The method of clause 57 or clause 58, wherein at least one of the electrodes overlays the saphenous nerve or its branches.

Clause 62: The method of clause 57 or clause 58, wherein at least one of the electrodes overlays the sural nerve or its branches.

Clause 63: The method of any of clauses 51-56, wherein the stimulation is applied through one or more electrodes on the skin on the patient's ankle.

Clause 64: The method of clause 63, wherein the one or more electrodes comprise a cathodal electrode and an anodal electrode.

Clause 65: The method of clause 63 or clause 64, wherein at least one of the electrodes overlays the sural nerve or its branches.

Clause 66: The method of clause 63 or clause 64, wherein at least one of the electrodes overlays the tibial nerve or its branches.

Clause 67: The method of any of clauses 51-56, wherein the stimulation is applied through one or more electrodes on the skin on the plantar surface of the patient's foot.

Clause 68: The method of clause 67, wherein the one or more electrodes comprise a cathodal electrode and an anodal electrode.

Clause 69: The method of clause 67 or clause 68, wherein at least one of the electrodes overlays the medial plantar nerve, lateral plantar nerve, or their branches.

Clause 70: The method of any of clauses 51-56, wherein the stimulation is applied through one or more electrodes on the skin on the patient's leg.

Clause 71: The method of clause 70, wherein the one or more electrodes comprise a cathodal electrode and an anodal electrode.

Clause 72: The method of clause 70 or clause 71, wherein at least one of the electrodes overlays the tibial nerve or its branches.

Clause 73: The method of clause 70 or clause 71, wherein at least one of the electrodes overlays the femoral cutaneous nerve or its branches.

Clause 74: The method of clause 70 or clause 71, wherein at least one of the electrodes overlays the saphenous nerve or its branches.

Clause 75: The method of clause 70 or clause 71, wherein at least one of the electrodes overlays the superficial peroneal nerve or its branches.

Clause 76: The method of clause 70 or clause 71, wherein at least one of the electrodes overlays the deep peroneal nerve or its branches.

Clause 77: The method of clause 70 or clause 71, wherein at least one of the electrodes overlays the sural nerve or its branches.

Clause 78: The method of any of clauses 51-56, wherein the stimulation is applied through one or more surgically implanted electrodes configured on or near one or more of the superficial peroneal nerve, the deep peroneal nerve, the saphenous nerve, the sural nerve, the tibial nerve, and/or the femoral cutaneous nerve.

While the present invention has been described in terms of the above examples and detailed description, those of ordinary skill will understand that alterations may be made within the spirit of the invention. Accordingly, the above should not be considered limiting, and the scope of the invention is defined by the appended claims.

The invention claimed is:

1. A method of treating underactive bladder in a patient by causing contraction of the bladder increasing bladder sensation, eliciting voiding to treat underactive bladder or urinary retention, increasing bowel sensation, or eliciting defecation to treat infrequent bowel movements or constipation in a patient in need thereof, comprising stimulating a peripheral nerve of a patient with electrical stimulation comprising pulses having a pulsewidth of 0.01 ms to 3 ms and intensity of greater than 0T and less than 5T, where T is a threshold intensity to induce a muscle twitch, and wherein the pulses are delivered at a frequency of 0.5 Hz to 3 Hz, thereby causing contraction of the bladder and treating underactive bladder in the patient,
   wherein the stimulation is applied through one or more surgically implanted electrodes configured on or near one or more of the superficial peroneal nerve, the deep peroneal nerve, the saphenous nerve, the sural nerve, the tibial nerve, and/or the femoral cutaneous nerve.

2. The method of claim 1, wherein the stimulation comprises electrical pulses having a pulsewidth of 0.2 ms and intensity of 1T to 2T, and wherein the pulses are delivered at a frequency of 1 Hz to 2 Hz.

3. The method of claim 1, wherein the stimulation comprises electrical pulses having a pulsewidth of 0.2 ms and intensity of 1T, and wherein the pulses are delivered at a frequency of 1 Hz.

4. The method of claim 1, wherein the stimulation comprises electrical pulses having a pulsewidth of 0.2 ms and intensity of 1T, and wherein the pulses are delivered at a frequency of 2 Hz.

5. The method of claim 1, wherein the stimulation comprises electrical pulses having a pulsewidth of 0.2 ms and intensity of 2T, and wherein the pulses are delivered at a frequency of 1 Hz.

6. The method of claim 1, wherein the stimulation comprises electrical pulses having a pulsewidth of 0.2 ms and intensity of 2T, and wherein the pulses are delivered at a frequency of 2 Hz.

7. A method of treating underactive bladder in a patient by causing contraction of the bladder, comprising stimulating a peripheral nerve of a patient with electrical stimulation comprising pulses having a pulsewidth of 0.01 ms to 3 ms and intensity of greater than 0T and less than 5T, where T is a threshold intensity to induce a muscle twitch, and wherein the pulses are delivered at a frequency of 0.5 Hz to 3 Hz, thereby causing contraction of the bladder and treating underactive bladder in the patient,
   wherein the stimulation is applied through one or more skin surface electrodes arranged on the patient's foot and/or leg.

8. The method of claim 7, wherein the stimulation is applied through one or more electrodes on the skin on the dorsal surface of the patient's foot.

9. The method of claim 7, wherein at least one of the electrodes overlays the superficial peroneal nerve or its branches.

10. The method of claim 7, wherein at least one of the electrodes overlays the deep peroneal nerve or its branches.

11. The method of claim 7, wherein at least one of the electrodes overlays the saphenous nerve or its branches.

12. The method of claim 7, wherein at least one of the electrodes overlays the sural nerve or its branches.

13. The method of claim 7, wherein the stimulation is applied through one or more electrodes on the skin on the patient's ankle.

14. The method of claim 7, wherein at least one of the electrodes overlays the sural nerve or its branches.

15. The method of claim 7, wherein at least one of the electrodes overlays the tibial nerve or its branches.

16. The method of claim 7, wherein the stimulation is applied through one or more electrodes on the skin on the plantar surface of the patient's foot.

17. The method of claim 7, wherein at least one of the electrodes overlays the medial plantar nerve, lateral plantar nerve, or their branches.

18. The method of claim 7, wherein the stimulation is applied through one or more electrodes on the skin on the patient's leg.

19. The method of claim 7, wherein at least one of the electrodes overlays the tibial nerve or its branches.

20. The method of claim 7, wherein at least one of the electrodes overlays the femoral cutaneous nerve or its branches.

* * * * *